US012699281B2

(12) United States Patent
Altmann et al.

(10) Patent No.: US 12,699,281 B2
(45) Date of Patent: Aug. 4, 2026

(54) EYEWEAR FOR ELICITING A BLINK RESPONSE AND MEASUREMENT SYSTEM THEREOF

(71) Applicant: HOYA Optical Labs of America, Inc., Lewisville, TX (US)

(72) Inventors: Griff Altmann, Ramsey, MN (US); Michael Marshall, Ramsey, MN (US); Suvagata Tripathi, Ramsey, MN (US); Joshua Miller, Ramsey, MN (US); Marga Acevedo, Ramsey, MN (US); Craig Drury, Ramsey, MN (US); Mehran Jaberzadeh, Ramsey, MN (US)

(73) Assignee: HOYA Optical Labs of America, Inc., Lewisville, TX (US)

( * ) Notice: Subject to any disclaimer, the term of this patent is extended or adjusted under 35 U.S.C. 154(b) by 294 days.

(21) Appl. No.: 18/504,998

(22) Filed: Nov. 8, 2023

(65) Prior Publication Data

US 2024/0148599 A1     May 9, 2024

Related U.S. Application Data

(60) Provisional application No. 63/580,328, filed on Sep. 1, 2023, provisional application No. 63/382,829, filed on Nov. 8, 2022.

(51) Int. Cl.
G02C 7/02 (2006.01)
A61H 5/00 (2006.01)
(Continued)

(52) U.S. Cl.
CPC ................ G02C 7/02 (2013.01); A61H 5/00 (2013.01); G02C 7/08 (2013.01); G02C 11/10 (2013.01);
(Continued)

(58) Field of Classification Search
None
See application file for complete search history.

(56) References Cited

U.S. PATENT DOCUMENTS

| | | | |
|---|---|---|---|
| 5,430,505 A | 7/1995 | Katz | |
| 8,994,885 B2 * | 3/2015 | Ando | G02C 7/083 |
| | | | 349/13 |

(Continued)

OTHER PUBLICATIONS

Spierer, A. et al., "Treating Amblyopia with LC Glasses: A Pilot Study," *Investigative Ophthalmology & Visual Science*, vol. 51, No. 7, Association for Research in Vision and Ophthalmology Jul. 2010, 4 pages.

(Continued)

*Primary Examiner* — Darryl J Collins
(74) *Attorney, Agent, or Firm* — Inskeep IP Group, Inc.

(57) ABSTRACT

A device may create an optical obstruction such as a haze for a predetermined amount of time in front of one or more eyes of the user and thereby trigger a blink response in the user. The device may include a lens having a plurality of layers and a sensor configured to detect a blink it at least one eye. At least one of the plurality of layers may include an electrodynamic layer in communication with the sensor. The electrodynamic layer may be configured to adjust the lens from a first state to a second state in response to a first signal from the sensor and from the second state back to the first state in response to a second signal from the sensor. The second state may include an at least partial obstruction of vision through the lens.

19 Claims, 11 Drawing Sheets

(51) Int. Cl.
    *G02C 7/08*        (2006.01)
    *G02C 11/00*     (2006.01)
    *A61B 5/11*       (2006.01)

(52) U.S. Cl.
    CPC ..... *A61B 5/1103* (2013.01); *A61H 2201/1604*
        (2013.01); *A61H 2201/165* (2013.01); *A61H*
        *2201/5092* (2013.01)

(56) References Cited

U.S. PATENT DOCUMENTS

| | | | |
|---|---|---|---|
| 10,437,327 B2 | 10/2019 | Sengelaub et al. | |
| 10,528,127 B2 | 1/2020 | Caraffi et al. | |
| 10,852,531 B2 | 12/2020 | Ryan et al. | |
| 11,181,740 B1 * | 11/2021 | Lewis ................ | G02B 27/0018 |
| 11,256,327 B2 | 2/2022 | Lundberg et al. | |
| 2013/0127980 A1 | 5/2013 | Haddick et al. | |
| 2016/0270656 A1 | 9/2016 | Samec et al. | |
| 2021/0181514 A1 | 6/2021 | Martin et al. | |

OTHER PUBLICATIONS

WIPO, U.S. International Search Authority, International Search Report and Written Opinion mailed Apr. 26, 2024 in International Patent Application No. PCT/US2023/079131, 10 pages.

\* cited by examiner

| Response Time, off → on (ms) | Initial | Molded |
|---|---|---|
| RF4 | 20 | 7 |
| Response Time, on → off (ms) | Initial | Molded |
| RF4 | 461 | 352 |

Response time before and after molding

FIG. 12

| Sample | Response Time, Off → On (ms) | Response Time, On → Off (ms) |
|---|---|---|
| RF1 initial | 7 | 391 |
| RF1 molded | 8 | 576 |

FIG. 14

EYEWEAR FOR ELICITING A BLINK RESPONSE AND MEASUREMENT SYSTEM THEREOF

RELATED APPLICATIONS

This application claims priority to U.S. Provisional Application Ser. No. 63/580,328 filed Sep. 1, 2023 entitled Eyewear For Eliciting A Blink Response And Measurement System Thereof, which claims benefit of and priority to U.S. Provisional Application Ser. No. 63/382,829 filed Nov. 8, 2022 entitled Eyewear For Eliciting A Blink Response And Measurement System Thereof, both of which are hereby incorporated herein by reference in their entireties.

BACKGROUND OF THE INVENTION

One common eye disorder is dry eye syndrome, also known as keratoconjunctivitis sicca, which is the condition of having dry eyes. Other associated symptoms include irritation, redness, discharge, blurred vision, and easily fatigued eyes.

Tears are produced by lacrimal glands located above your eyes and spread across the surface of the eye when blinking. They then drain into small holes in the corners of your upper and lower lids before traveling through small channels and down your tear ducts to your nose.

Typically, dry eye syndrome occurs when either the eye does not produce enough tears or when the tears evaporate too quickly. This can result from a range of causes, such as contact lens use, meibomian gland dysfunction, pregnancy, Sjögren syndrome, vitamin A deficiency, omega-3 fatty acid deficiency, LASIK surgery, and certain medications such as antihistamines, some blood pressure medication, hormone replacement therapy, and antidepressants. Treatment for dry eye syndrome depends on the underlying cause. Artificial tears are typically the first line of treatment.

Healthy individuals typically blink about 10-15 times per minute. With each blink, the eye's tear film is renewed, which protects and moisturizes the eye. The tear film consists of three sublayers: mucus, watery and oil layer at the top, which protects the eye from dryness (water evaporation).

Because blinking coats the eye with tears, dry eye syndrome symptoms are typically worsened by activities in which the rate of blinking is reduced due to prolonged use of the eyes. These activities include prolonged reading, computer usage (computer vision syndrome), driving, or watching television. Hence, it can be beneficial to increase an individual's rate of blinking to help prevent dry eye syndrome and similar disorders.

Amblyopia is a disorder of sight in which the brain fails to fully process input from one eye and over time favors the other eye. It results in decreased vision in an eye that typically appears normal in other respects. Amblyopia is the most common cause of decreased vision in a single eye among children and younger adults.

The cause of amblyopia can be any condition that interferes with focusing, typically during early childhood. This can occur from poor alignment of the eyes (strabismic), an eye being irregularly shaped such that focusing is difficult, one eye being more nearsighted or farsighted than the other (refractive) or clouding of the lens of an eye (deprivational).

Amblyopia typically has three main causes: strabismic (misaligned eyes), refractive (difference of a certain degree of nearsightedness, farsightedness, or astigmatism) or by significant amount of equal refractive error in both eyes, or deprivational by deprivation of vision early in life by vision-obstructing disorders such as congenital cataract.

Strabismic amblyopia and refractive amblyopia are typically treated by clarifying the visual image with glasses or encouraging use of the amblyopic eye with an eyepatch over the dominant eye or pharmacologic penalization of the better eye. Penalization usually consists of applying atropine drops to temporarily paralyze the accommodation reflex, leading to the blurring of vision in the good eye. It also dilates the pupil. This helps to prevent the bullying and teasing associated with wearing a patch, although sometimes application of the eye drops is challenging.

SUMMARY OF THE INVENTION

The present invention is directed to devices and methods for eliciting a blink response in a patient/user. Generally, this blink response is caused by creating a temporary shade, haze, blur, or similar optical feature (referred herein after as haze for simplicity) in front of a user's eyes, which thereby induces the user to blink. When a tear film in the eye breaks, a blur is created. The brain detects the haze and triggers a blink, so that the tear film on the eye is rebuilt. The devices of the present invention seeks to mimic this haze to trigger the brain in eliciting a blink response at any given time (e.g., at regular intervals, irregular intervals, or based on sensor data).

The temporary haze may be created on several different devices, such as on eyeglasses, computer monitors, televisions, or similar displays. The haze may be electronically activated and connected to an electronic controller that controls when the haze is temporarily activated. The electronic controller may be a microprocessor, microcontroller, computer, or similar processing device on, embedded in, or near the device. The electronic controller may also be connected to or may further be an electronic switch or a phone in wired/wireless communication with a processor (e.g., a processor that is part of eyeglasses).

Part of the electronic controller may also include a device for monitoring whether a patient's eyes are open or blinking. This may be accomplished by one or more cameras that monitor one or more eyes and a processor that determines, based on the camera's video footage, when an eye is open or closed. Such a camera may be included as part of eyeglasses (e.g., on an eyeglass frame) or at a separate location (e.g., near a computer monitor). In one example, the processor determines the state of a monitored eye by determining if the top and/or bottom portions/perimeters of the eye are relatively curved or arc shaped (e.g., the eye is open) or relatively straight (e.g., the eye is closed).

A device for triggering a blink response can include a sensor configured to detect a blink in at least one eye and a lens including a plurality of layers comprising an electrodynamic layer in communication with the sensor. The electrodynamic layer is configured to adjust the lens between a first state and a second state in response to a first signal by the sensor and adjust the lens between the second state and the first state in response to a second signal by the sensor.

A system for triggering a blink response can include a sensor configured to detect a blink in at least one eye, a lens including a plurality of layers, and a controller in communication with the sensor. At least one of the plurality of layers includes an electrodynamic layer in communication with the sensor; and the electrodynamic layer is configured to adjust a lens between a first state and a second state in response to a first signal and adjust the lens between the second state and the first state in response to a second signal.

The controller is configured to generate the first signal and the second signal based on signal communication with the sensor.

A method of inducing a blink response can include adjusting an electrodynamic layer of a lens between a first state and a second state in response to a first signal by a sensor configured to detect a blink in at least one eye; and, adjusting the lens between the second state and the first state in response to a second signal by the sensor.

A device for triggering a blink response that may act as an alternative to a permanent patch (e.g., Bangerter filters such as Bangerter occlusion foils) or atropine penalization. The device may be used to produce a predetermined level of haze so as to function as a patch to treat amblyopia. An optical obstruction (e.g., haze) may be produced on demand. The type of optical obstruction may include a predetermined level or a suite of levels.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 12 is a table showing response times of an electro-dynamic layer before and after molding of a lens stack, in accordance with an example embodiment.

FIG. 14 is a table showing haze of liquid crystal laminates made with moisture cured adhesive before and after molding of a lens stack, in accordance with an example embodiment.

DETAILED DESCRIPTION

Figure 1:
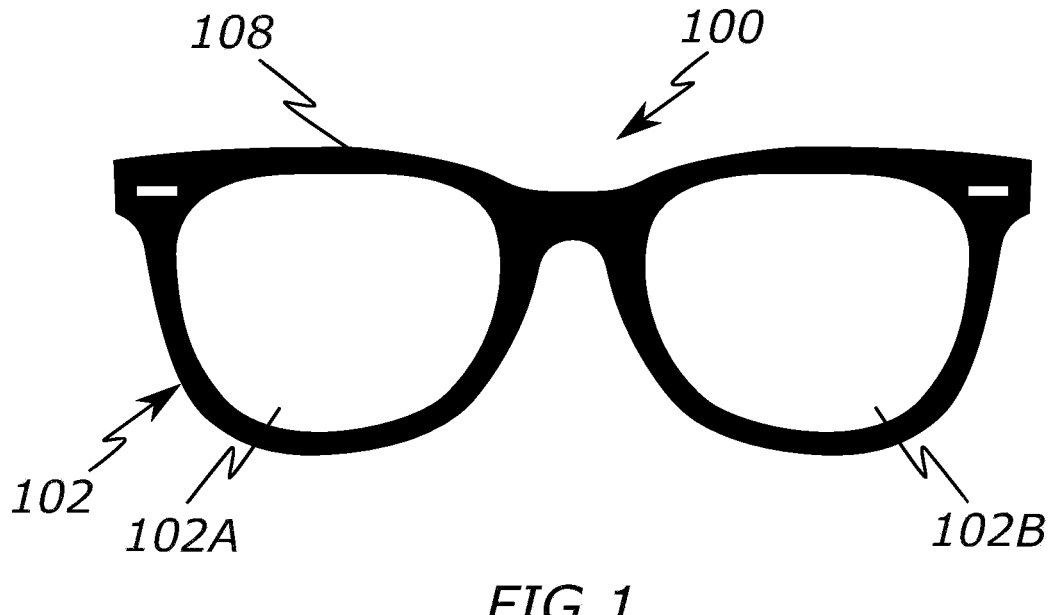
FIGS. 1 and 2 illustrate eyeglasses that may selectively create haze in its lenses to induce a blink response in accordance with an example embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

While different embodiments may be described in this specification, it is specifically contemplated that any of the features from different embodiments can be combined together in any combination. In other words, the features of different embodiments can be mixed and matched with each other. Hence, while every permutation of features from different embodiments may not be explicitly shown, it is the intention of this specification to cover any such combinations.

Disclosed herein are devices, systems, and methods for eliciting a blink response in a patient/user or creating an optical obstruction (e.g., a blur) that is equivalent to a patch and thereby treating various eye conditions or deficiencies. Generally, this blink response is caused by creating an optical obstruction such as temporary shade, haze, blur, or similar optical feature (referred herein after as haze for simplicity) in front of a user's eyes, which thereby induces the user to blink.

The temporary haze may be created on several different devices, such as on eyeglasses, computer monitors, televisions, or similar displays. Thus, the optical obstruction may be formed in various devices having screens or lenses, including but not limited to various monitors, televisions, glasses, contact lenses, and the like as discussed below.

The optical obstruction (e.g., haze) may be electronically activated and connected to an electronic controller that controls, modulates, or activates (which are all generally used synonymously in this specification) when the optical obstruction is periodically and temporarily activated. The electronic controller may be a microprocessor, microcontroller, computer, or similar processing device on, embedded in, or near the device. The electronic controller may also be connected to or may further be an electronic switch or a phone in wired/wireless communication with a processor (e.g., a processor that is part of eyeglasses).

Part of the electronic controller may also include a device for monitoring whether a patient's eyes are open, closed, and/or blinking. This may be accomplished by one or more cameras that monitor one or more eyes and a processor that determines, based on the camera's video footage, when an eye is open or closed. Such a camera may be included as part of eyeglasses (e.g., on an eyeglass frame) or at a separate location (e.g., near a computer monitor). In one example, the processor may determine the state of a monitored eye by determining if the top and/or bottom portions/perimeters of the eye are relatively curved or arc shaped (e.g., the eye is open) or relatively straight (e.g., the eye is closed).

In some examples, the electronic controller or control system can be configured to maintain the optical obstruction in front of the patient or user for a predetermined time interval that is sufficient or adequate to trigger a blink reaction or response in at least one eye of the patient or user (e.g., a relatively short period of time). For example, the electronic controller can send a first signal to a lens or a screen in front of the patient or user to adjust the lenses or screen from a first state to a second state (e.g., a hazy, cloudy, blurry, or other at least partially obscured state).

The electronic controller can, using sensors monitor the eyes of the patient or user, determine whether the user has blinked in response to the adjustment of the lenses or screen from the first state to the second state. If the user has blinked, the electronic controller can adjust the lenses or screen from the second state back to the first state (e.g., a clear or transparent state). In this way, the electronic controller, the sensors, and the lenses or screen in front of the patient or user can form a closed feedback loop operable to ensure the patient or user has blinked a desired number of times during a predetermined time period or time interval.

In that respect, a method of use also includes monitoring an eye for one or more blinks over a predetermined period of time, determining that fewer than a predetermined number of blinks have occurred during the predetermined period of time, modulating an optical obstruction on a device in front of the eye (e.g., eyeglasses or screen) to generate a blink, and removing the haze from the device. The causing of haze may further include applying voltage to a liquid crystal laminate (or similar display) on or in the device for a predetermined period of time.

The electronic controller may also adjust how frequently a blink response is induced (e.g., adjust the predetermined time and/or the number of predetermined blinks that should occur) based on a feedback system. The blink response may be induced regardless of whether the user is blinking at an acceptable rate (e.g., if the user's eyes are not monitored) or the blink response may be induced at a specific rate only if the user does not meet a certain threshold.

The frequency of the induced blink response of the feedback system may be user adjustable from an application allowing the user to adjust the rate that an optical obstruction is modulated (i.e., a blink response is triggered or elicited). The user may determine a specific rate or may select certain activities that have predetermined blink rates associated with them (e.g., viewing a monitor, viewing a TV, viewing distant objects).

In another example, frequency of the induced blink response of the feedback system may be based on sensor feedback, such as cameras or other sensors. The data from these sensors may allow the feedback system to determine whether the data is above or below certain thresholds and then either increase or decrease the frequency of the induced blink response (either accounting for the user's actual blinks or without regard for the user's actual blinks if no eye tracking sensor is present). Example sensor data may include depth of field, colors being viewed by the user, light intensity, rate of change of the user's visual stimulus (e.g., fast moving images), and ambient humidity. If the blink inducing device includes eyeglasses, it may be desirable to include such sensors on the glasses themselves, such as a forward-facing camera away from the user's face or a humidity sensor.

Moreover, in some examples, by monitoring the eyes of the patient or user through the sensors, the electronic controller may determine that fewer than the desired or a predetermined number of blinks have occurred over the predetermined time period or time interval. In response, the electronic controller can modulate or control the optical obstruction in front of the eyes of the patient or user to increase a blink rate, such as a normal blink rate or a blink rate observed during certain activities, of the patient or user, such as by shortening a time interval between the periodic appearance of the optical obstruction.

In further examples, the electronic controller can be configured to maintain the optical obstruction in front of at least one eye of a user or patient for relatively longer period of time (e.g., minutes, hours, or days), such as to help treat some types of Amblyopia. For example, by maintaining the optical obstruction in front of a dominant (e.g., amblyopic) eye of the patient or user while allowing clear vision in front of a less dominant (e.g., normal) eye of the patient or user, use of the amblyopic eye can be encouraged without atropine drop application or an eyepatch to penalize the dominant eye.

The device may create haze via electronically controlled haze-inducing techniques, such as a liquid crystal laminate. Such a liquid crystal laminate may have at least one pixel or at least one pixel per eye in the case of eyeglass devices. However, multiple pixels may also be used.

The blink inducing device (e.g., eyeglasses, monitor screen, or the like) may create haze in front of a user's eyes relatively quickly or may more slowly increase and/or decrease the haze level to more reliably induce a blink response. For example, the haze may be created and maintained for 0.1 second to 1 second for a generally quick optical obstruction that is created, or may be created and maintained in a relatively longer time frame, such as between 1 second and 10 seconds. In a more specific example, the haze may be maintained in about 0.1, 0.2, 0.3, 0.4, 0.5, 0.6, 0.7, 0.8, 0.9, 1, 2, 3, 4, 5, 6, 7, 8, 9, or 10 seconds (as well as increments in between).

During whatever time interval that is chosen, the haze may be increased and decreased. The time of increasing and decreasing the haze may be equal (e.g., 1 second increasing and 1 second decreasing) or it may not be equal (e.g., 1 second increasing and 0.1 seconds decreasing). The decreasing in haze may also be determined by a detection of a blink. For example, the level of haze may be slowly increased (i.e., light transmittance can be slowly decreased) but if a blink of the user is detected, the device immediately removes the haze (i.e., light transmittance immediately increases to a relatively clear state).

Additionally, the amount of haze created can be varied based on user preference (e.g., set from a computer or phone app) or based on sensor data (e.g., based on the intensity of light in the user's environment). For example, in lower light situations around a user, a lower haze level might be desirable (e.g., 40% transmittance) and in brighter light situations, a higher haze level might be desirable (e.g., 20% transmittance).

Additionally, a predetermined level of an optical obstruction (e.g., haze) can be created and maintained until turned off or disabled by a user, thus mimicking a Bangerter filter. Such use may function as an alternative to permanent patching of an eye.

In view of the above, the devices and systems of the present disclosure can be used to help to relieve, prevent, or otherwise address various eye conditions associated with an insufficient or low blink rate caused by inadequate activity in the muscles responsible for blinking, such as, but not limited to, dry eye syndrome.

Specific embodiments and aspects of embodiments will now be discussed. However, it should be understood that these embodiments are examples of the previous discussion. Hence, any of the previously discussed aspects, variations, and examples may, not only be combined with each other, but may also be combined with the specific embodiments described below.

Figure 2:
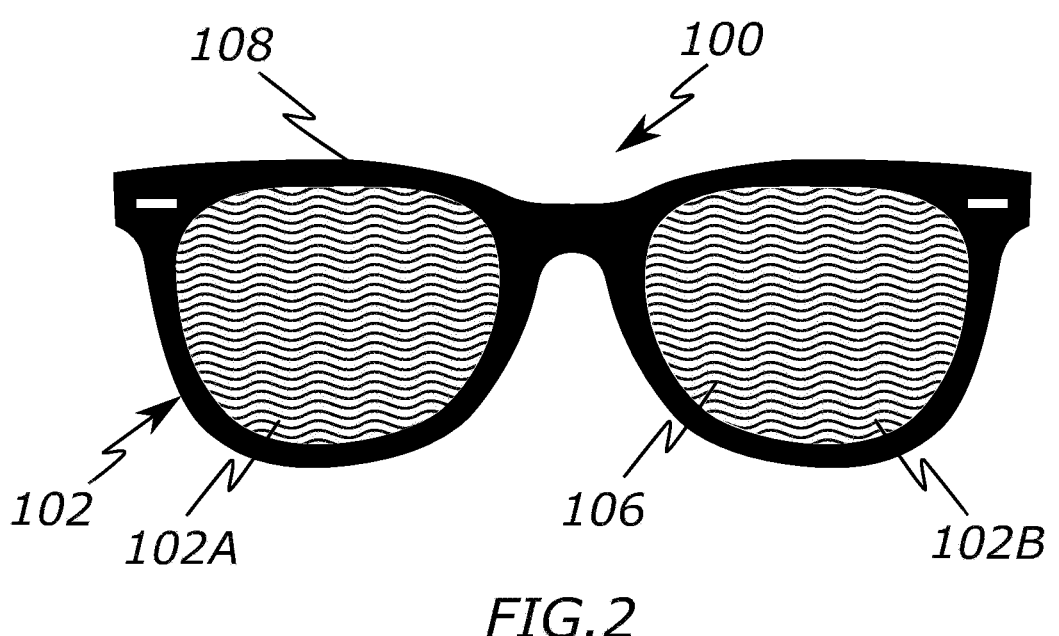

FIGS. 1 and 2 illustrate eyeglasses 100 that may selectively create an optical obstruction (e.g., a haze) in one or both of its lenses 102 to induce a blink response. Again, while the term haze may be used in this specification, this term may also be understood to mean various types of optical obstructions, such as shading, darkening, or otherwise adjusting the transmittance or focus of light through an optical element. The eyeglasses 100 may include a frame 108 that is shaped and sized to receive and retain a pair of lenses 102 including a first lens 102A and a second lens 102B, as well as fit on a user's face. One or both of the first lens 102A and/or second lens 102B of the lenses 102 may be adjustable between, or can otherwise define, have, or include, a first state and a second state.

In the first state, such as shown in FIG. 1, one or both of the lenses 102 may be relatively clear or transparent so as not to obstruct vision of a user wearing the eyeglasses 100. As an example, in the first state, one or both of the lenses 102 may allow between about 90% and 100% light transmittance to pass therethrough.

In the second state, such as shown FIG. 2, one or both of the lenses 102 may create an optical obstruction, such as by being at least partially obscured. As an example, in the second state, one or both of the lenses 102 may create or display a hazing effect, a shading effect, or a blurring effect, and as such, can appear to a user as relatively or completely hazy, shaded, or blurred. In some examples, the second state may be defined as a reduced percentage of light transmittance (e.g., an amount of haze or obstruction), such as, but not limited to, between about 10%-30% reduction of light transmittance, between about 31%-50% reduction of light transmittance, between about 51%-70% reduction in light transmittance, or between about 71%-100% reduction in light transmittance, through one or both of the lenses 102.

In any such examples, the amount or percentage of light transmittance reduction through one or both of the lenses 102 in the second state, relative to the first state, may be suitable or sufficient to trigger a blink response in a user. In various examples, the second state (e.g., the optical obstruction, haze, hazing, blurring, shading, and the like) may be created in only one of the first lens 102A and the second lens 102B, both of the first and second lenses 102A, 102B simultaneously, and/or in both of the lenses 102 independently at different times.

The lenses 102 may generally be formed or manufactured in a way that includes a material that, when voltage is applied (or if voltage is no longer applied), transitions from the first state to the second state becoming hazy, dark, opaque, or otherwise allowing a reduced percentage of light transmittance therethrough. In one such example, the second state (e.g., a hazy or blurred state) may be created by a haze-inducing layer 106 located on, within, or otherwise between various individual layers or a plurality of layers forming each of the lenses 102.

The creation or appearance of the optical obstruction (e.g., the haze or second state) in the first lens 102A and/or the second lens 102B may be modulated, actuated, activated, or otherwise controlled by an electronic controller (e.g., a processor or processing device, microprocessor, or microcontroller) in electrical communication with the lenses 102. Such a controller can be electrically connected to, or can be in electrical or conductive communication with, the haze-inducing layer 106 within the first lens 102A and the second lens 102B, such as via one or more electrical contacts or connection points.

This can allow the controller to, for example, selectively apply current or power (e.g., a voltage or voltage signal) to the first lens 102A or the second lens 102B, such as either simultaneously or at different times, to activate the haze or hazing effect (e.g., adjust the first lens 102A or the second lens 102B to the second state), selectively control or modulate when the first lens 102A or the second lens 102B become hazy (e.g., adjust or transition from the first state to the second state), how long they remain hazy (e.g., how long the second state is maintained), the level of haze created therein (e.g., the percentage of light transmittance reduction observed during the second state), or other factors or parameters associated with an electrically modulated optical obstruction.

In some examples, the frame 108 of the pair of eyeglasses 100 may include the controller, which can include a processor or processing device, a microprocessor, or microcontroller, and a power supply (e.g., a battery or transformer). In some examples, the controller, included various components thereof, may be embedded, molded, cast, or otherwise integrated into the frame 108 of the pair of eyeglasses 100. In other examples, the controller, including various components thereof, can be affixed or connected to an exterior or outer surface of the frame 108. In alternative examples, the controller, including any of various components thereof, may be partially or completely separate from the frame 108 and in electrical communication with, or otherwise connected to, the haze-inducing layer 106 of the lenses 102 via wired or wireless signals to at least one component of the controller located on or within the pair of eyeglasses 100.

Irrespective of whether the controller, or any of various components thereof, is part of the pair of eyeglasses 100 or is separate from the pair of eyeglasses 100, various parameters or factors associated with when and how the pair of eyeglasses 100 create a haze or optical obstruction in the lenses 102 (e.g., adjust the first lens 102A or the second lens 102B from the first state to the second state) may be controlled using various methods, or otherwise controlled in a number of different ways, such as further discussed below with reference to any of FIGS. 3-14.

As seen in FIG. 1, the eyeglasses 100 may have a first state in which one or more of the lenses 102 have a relatively clear state to the user/wearer. As seen in FIG. 2, the eyeglasses 100 may also have a second state in which one or more lenses 102 have a relatively hazy state. The hazy state may be created in only one lens 102, both lenses simultaneously, and/or both lenses independently at different times. The haze may be created by a haze-inducing layer 106 on or between layers of the lenses 102. For example, the haze-inducing layer 106 may be a PET laminate, polycarbonate laminate, nylon laminate, polyimide laminate, biaxially oriented PET triacetate laminate, or polarized sheet laminate containing a liquid crystal film layer such as a polymer-dispersed liquid crystal film (PDLC) layer. In the example of eyeglasses 100, the haze-inducing layer 106 (e.g., the liquid crystal laminate) may be further formed into lenses, such as via an injection molding process in which the lenses 102 may optionally be curved to impart a corrective prescription.

The frame 108 of the eyeglasses 100 may include a controller (e.g., a processor, microprocessor, or microcontroller), as well as a power supply (e.g., a battery), that is electrically connected to each of the lenses 102A, 102B. This allows the controller to control when the lenses 102A, 102B become hazy, how long they remain hazy, and the level of haze created (e.g., light transmittance). For example, the controller may selectively apply power to each lens 102A, 102B (either simultaneously or at different times) to activate the haze. This controller may be embedded in the frame 108 or connected to an exterior of the frame. Alternately, the controller may be separate from the frame and connected via wire or wireless signals to the eyeglasses 100.

Figure 3:
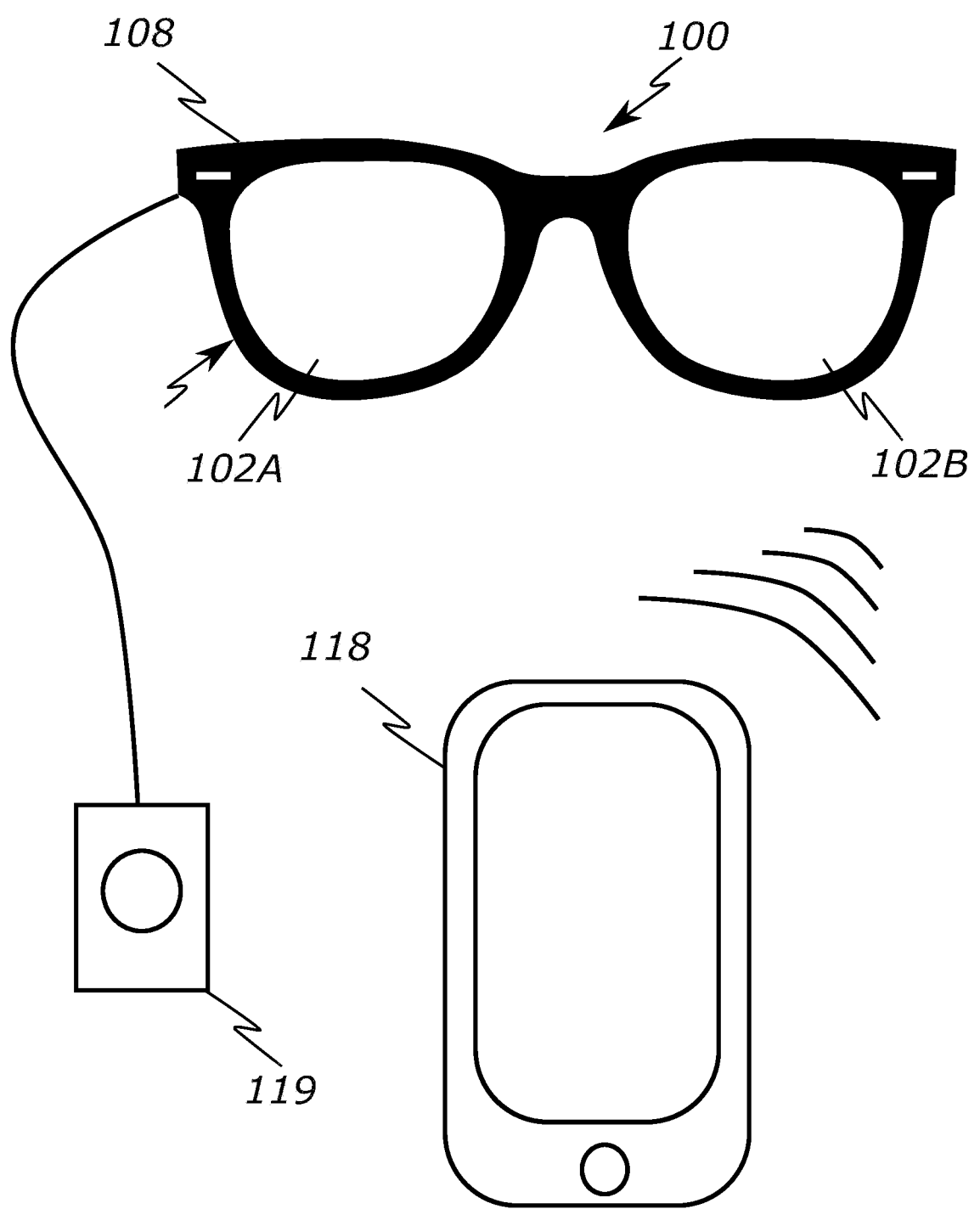
FIG. 3 illustrates a separate user interface mechanism that may be connected to the eyeglasses by wire or wireless mechanisms in accordance with an example embodiment.

Whether the controller is part of the eyeglasses 100 or separate from them, parameters of when and how the eyeglasses 100 create haze to induce a blink response may be controlled in several ways. As seen in FIG. 3, a separate user interface mechanism 119 may be connected to the eyeglass frame 108 by wire or wireless mechanisms. The interface mechanism may include a button, knob, or similar inputs and optionally a display so that a user can either immediately actuate the haze or can adjust parameters of when the haze occurs (e.g., time between haze, percent haze/transmissibility, time that haze is displayed for each blink, etc.). Alternately, the same interface controls may be included on an app of a smartphone 118, which may communicate wirelessly with a wireless communication interface on/in the eyeglasses 100.

FIG. 3 illustrates an example user interface 119 connectable to the pair of eyeglasses 100 of FIGS. 1-2, in accordance with at least one embodiment of the present disclosure. As illustrated in FIG. 3, the user interface 119 can be realized in the form of, or can be displayed on, a separate user interface mechanism or device connected to, or in communication with, the frame 108 of the pair of eyeglasses 100, such as via various wired or wireless means.

In some examples, the user interface 119 may include, but not limited to, any of one or more buttons, knobs, switches, keys, other physical input devices or features. In some examples, such input devices or features of the user interface 119 may be realized virtually in the form of visual interface displayed by a mobile application or other applications or software, such as on a mobile or smart phone, an electronic table, or desktop or laptop computer. In some such examples, the user interface 119 can be operable or otherwise usable or engageable via a touch sensitive display.

The user interface 119 can be configured to enable a user or patient to select or selectively adjust, among others, any of various parameters, factors, or settings associated with the appearance of the optical obstruction in the lenses 102 (e.g., the second state of the first lens 102A or the second lens 102B). For example, the user or patient can engage with the controller via the user interface 119, such as via one or more user inputs thereto, to choose to, among others, immediately actuate the haze (e.g., cause the first lens 102A or the second lens 102B to transition from the first state to the second state); or, adjust various parameters of when the haze occurs, such as a time interval between periodic hazing of the lenses 102 (e.g., the time interval between the first lens 102A or the second lens 102B transitioning from the second state to the first state, and then back to the second state from the first state hazing of the lenses 102), a percent haze or transmissibility (e.g., the percentage of light transmittance reduction in the second state), or a time period that haze is displayed or maintained on the lenses 102 (e.g., the length of time the first lens 102A or the second lens 102B remain in the second state).

Figure 4:
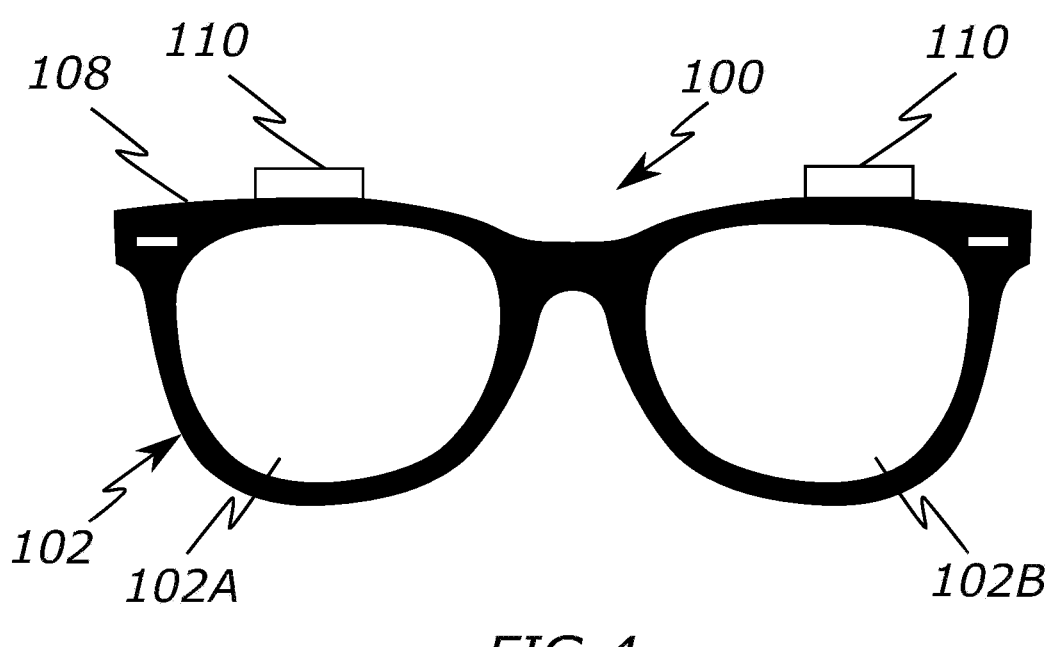
FIG. 4 illustrates eyeglasses that may also include sensors that may be used to monitor various aspects of the user's eyes and/or the users surrounding environment in accordance with an example embodiment.
Figure 5:
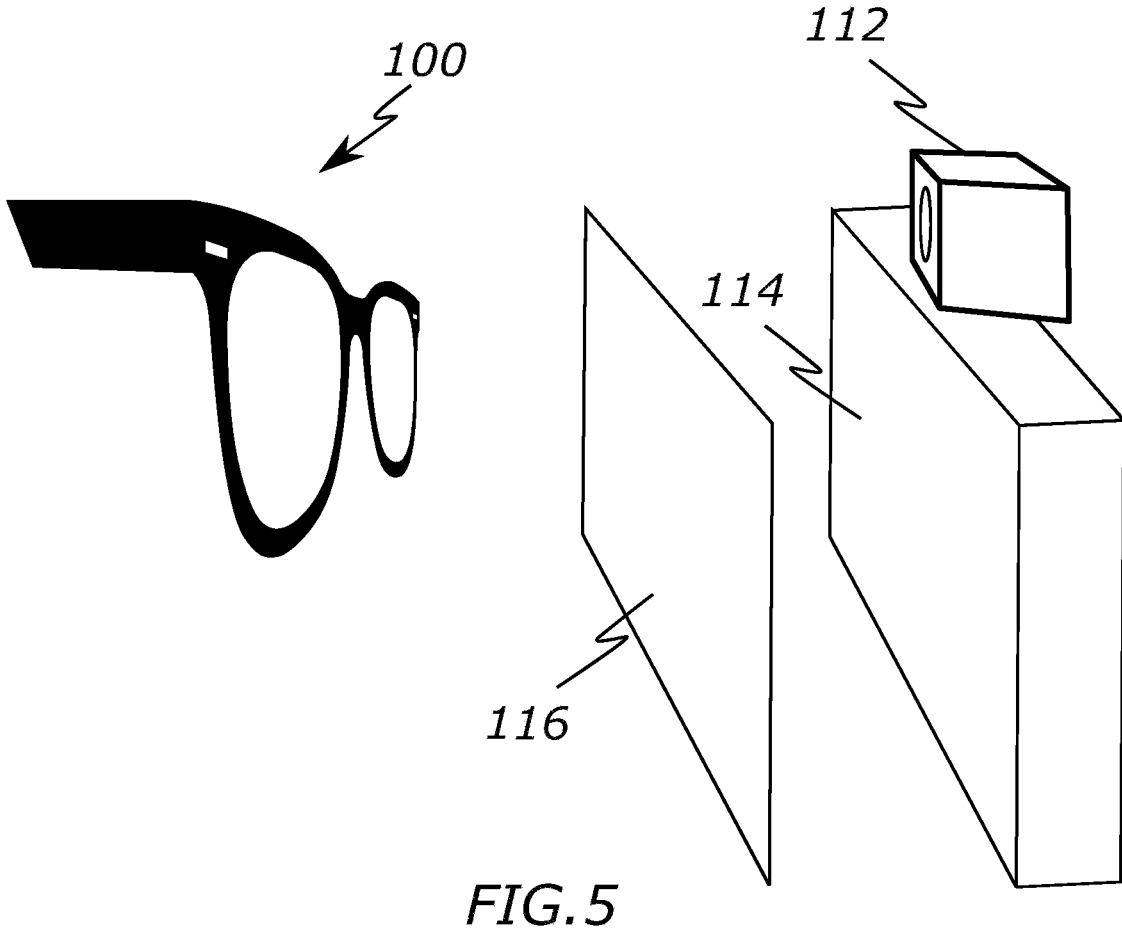
FIG. 5 illustrates another embodiment in which the haze is created on a film or screen in front of a monitor in accordance with an example embodiment.

FIG. 4. illustrates an example pair of eyeglasses 100 including sensors 110, and FIG. 5 illustrates an example pair of eyeglasses 100 positioned in front of a monitor 114 and a screen 116. FIGS. 4-5 are discussed below concurrently. As shown in FIG. 4, the frame 108 of the pair of eyeglasses 100 may include the sensors 110, and as shown in FIG. 5, the monitor 114 can include the sensor 112.

The sensors 110 or the sensor 112 can each generally represent one, two, three, four, or other numbers of similar or different types of individual sensors. The sensors 110 or the sensor 112 may generally be used to monitor various aspects of one or more eyes of a patient or user, and/or various aspects of a surrounding environment of the patient or user. For example, one of more individual sensors of the sensors 110 or the sensor 112 can be, but is not limited to, a still image camera, a video camera, an optical sensor, an ambient light sensor, or an ambient humidity sensor.

In some examples, the sensors 110 and the sensor 112 can include one or more video cameras. In one such example, such as shown in FIG. 4, the sensors 110 can include two video or still-image cameras and/or optical sensors positioned with respect to and configured to monitor each eye of the user or patient. In such an example, the sensors 110 can be removably or fixedly positioned on, or otherwise integrated into or located within, the frame 108 of the pair of eyeglasses 100.

Further, in such an example, the sensors 110 can be positioned or located above or below the first lens 102A and the second lens 102B, such as on or within a top or bottom of the frame 108 and can each generally face or be angled toward each eye of the user or patient. Alternatively, the one or more of the sensors 110 may be placed on, integrated into, or located at sides (e.g., the legs or arms) of the frame 108 while still generally facing or being angled toward each eye of the user or patient. Such examples (e.g., examples including one of the sensors 110 for each eye) can allow each eye may to be monitored separately, and the haze (e.g., the transition from the first state or the second state) can accordingly controlled or otherwise modulated as desired independently between a first eye and a second eye of the user or patient.

In another example, the sensors 110 can include only a single sensor, which may be used to monitor only a single eye, or both eyes concurrently, of the patient or user, and the haze can accordingly be controlled in both of the first lens 102A and the second lens 102B concurrently (e.g., since eyes tend to blink together).

In some examples, such as shown in FIG. 5, the sensor 112 can be positioned or located at a separate location from the pair of eyeglasses 100, such as, but not limited to, on or near the monitor 114, the screen 116, or otherwise near any electronic displays viewable by the patient or user. In some such examples, the sensor 112 can be in wired or wireless communication with an electronic controller, such as including a processor or processing device and a power supply (e.g., a battery or transformer) connected or otherwise in communication with the screen 116.

In contrast to the pair of eyeglasses 100, the screen 116 can be a feature or component responsible for creating the optical obstruction (e.g., a haze inducing or electrodynamic layer). The screen 116 can generally be an internal or external film or layer made of including a material, such as film or layer, that when voltage is applied (or if voltage is no longer applied), can transition from the first state to the second state to become hazy, dark, opaque, semi-transparent, or otherwise allowing a reduced percentage of light transmittance therethrough. While the screen 116 is shown in FIG. 5 as positioned over a display of the monitor 114, it is to be appreciated that the screen 116 can be configured for attachment or positioning on, or can be integrated into, any display of any electronic device, such as mobile or smartphone which may or may not include the user interface 119 (FIG. 3).

In some examples, an entire surface area of the lenses 102 or the screen 116 may be configured as a single pixel. In such an example, when a voltage is applied to the lenses 102 or the screen 116 by the controller, the entire surface area of the lenses 102 can transition or be adjusted into the second state (e.g., can become hazy, blurred, or at least partially obstructed). Alternatively, in other examples, when a voltage is applied to the lenses 102 or the screen 116, only a portion of the surface area of the lenses 102 or the screen 116 may transition or be adjusted into to the second state, such as only a center area, only a peripheral area, or only smaller portions/patterns at the center and/or peripheral portions.

In some examples, the sensor 112 can be located within a threshold or maximum distance from the patient or user, such as predetermined, or otherwise known, to be suitable or otherwise effective to trigger a blink response in the patient or user when the screen 116 transitions from the first state to the second state (e.g., when the optical obstruction appears on the screen 116). Such a distance can be based on, among others, a size or surface area of the monitor 114 or the screen 116, the brightness level of the monitor 114 or the screen 116, or other variables.

In further examples, any of the screen 116, the monitor 114, or the sensor 112 can be in communication with various components of the pair of eyeglasses 100 via various wired or wireless means or mechanisms, such as, but not limited to, through the user interface 119 or one or more of various types of controllers, such as in an example where both the sensors 110 and the sensor 112 are used to monitor the eyes of the user or patient.

In some examples, the sensors 110 or the sensor 112 can include one or more cameras or optical sensors facing away from the eyes of a user or patient. Such sensors 110 or the sensor 112 may record video imaging data, or other types of data, that can be analyzed by the controller to determine, for example, but not limited to, a depth of field, colors or colors being view through the lenses 102 or the screen 16, ambient light or light intensity of the monitor 114, or a rate of change of a visual stimulus or visual stimuli the user or patient is viewing. Finally, any combination of the example sensors 110 or the sensor 112 discussed above or below may be used independently or in combination with one another.

The sensor data (e.g., the information obtained by the sensors 110 or the sensor 112) may generally be any type of data recordable or usable by the sensors 110 of the pair of eyeglasses 100 or the sensor 112, such as, but not limited to, video data monitor a user's eyes for blinking occurrences, still imaging data indicating a blinking occurrence, optical or electrical potential data indicating a blink occurrence, or ambient light or humidity data.

As such, in various examples, the sensor data can be used by the controller in a variety of ways for various purposes. In some examples, the controller can use the sensor data to determine or modulate various parameters associated with the creating the optical obstruction (e.g., a haze or hazing effect, a shade or shading effect, or a blur or blurring effect) in front of the patient or user via the first lens 102A, the second lens 102B, the screen 116, or other haze inducing or creating devices or systems and removing the optical obstruction in front of the patient or user via the first lens 102A, the second lens 102B, the screen 116, or other haze inducing or creating devices or systems from the first lens 102A, the second lens 102B, the screen 116, or other haze inducing or creating devices or systems.

For example, such parameters can be, but are not limited to, a frequency of the temporary optical obstruction (e.g., a time interval or period between two consecutive appearances of the second state or haze effect in the lenses 102 or the screen 116), the length of each appearance of the optical obstruction (e.g., how long the lenses 102 or the screen 116 are maintained in the second state), or the amount of light transmission during the appearance of the optical obstruction (e.g., the percentage of light transmittance reduction in the second state) using various methods or processes described above or below.

One such method or process can include causing the patient or user to blink by creating an optical obstruction in front of at least one eye of the patient of user, monitoring, via the sensing or sensor data, the at least one eye to confirm or verify when the patient or user blinks, and removing the temporary optical obstruction or haze from the lenses 102 or the screen 116 within a predetermined period of time or time interval after a blink or blink response.

In one such method or process, a processor of the controller can be configured to periodically or continuously determine or evaluate a state or position of the at least one eye of the patient or user by analyzing the sensor data from the sensors 110 or the sensor 112 to determine if one, or both, top or bottom portions or perimeters of the one or more eyes (e.g., the upper and lower eyelids thereof), are relatively curved or generally arc shaped, which can indicate that the one or more eyes are open, or are relatively straight or flat, which can indicate that the one or more eyes are closed. In view of the above, sensor data capturing the shape or position of the eyelids can be usable to monitor blink or blink response in one or more eyes of the patient or user.

In one such example methods or process, each of the sensors 110 or the sensor 112 may record video data analyzed by the controller to determine if each eye has blinked upon the appearance of the optical obstruction in the lenses 102 or the screen 116 (e.g., the transition or adjustment of the lenses 102 or the screen from the first state to the second state); and the controller can respond to the video data (e.g., blink data) in a relatively quick, or an instantaneous manner, to remove the temporary optical obstruction or haze from the lenses 102 or the screen 116 (e.g., by adjusting the lenses 102 or the screen 116 from the first state or a second state).

In another example method or process, the video data recorded by the sensors 110 or the sensor 112 may be received by the controller, but the controller may not cause the optical obstruction or haze to be removed from the lenses 102 or the screen 116 for a longer period (e.g., not instantaneously) of time, such as for various purposes. For example, the controller may determine that the patient or user has not blinked in response to the appearance of the optical obstruction, and in response, may increase the haze effect (e.g., by increasing the percentage of light transmittance reduction through the lenses 102 or the screen 116) until a user blinks, or otherwise maintain the optical obstruction in the lenses 102 or the screen 116 until the user blinks.

In some examples, the controller can be configured to store the video data (e.g., blink data), such as on an internal memory of the controller or on a external database, for a predetermined temporary period of time, or permanently, along with a timestamp for each observed blink. This can enable the patient or the user, or a healthcare provider, to review the blink data to determine, as well as assess, a blink frequency or blink rate of the patient or user, such as generally over various periods or lengths of time or during specific activities.

In some such examples, the number of blinks or blink events recorded or stored (which can be an exact numbers as recorded or processed number such as a calculated average number of blinks or blink events over many separate time periods or intervals), can be compared to a predetermined value or value range, such as a threshold value or value range. In some examples, such as threshold value or value range can be associated with a normal or adequate blink rate generally known to prevent or help address dry eye syndrome, or with a desired value or value range determined by a healthcare provider's recommendation or prescription for an individual patient.

In some such examples, such threshold value or value range can represent a normal or adequate blink rate based on Table 1 below. Table 1 describes examples of common or typical blink rates in some specific situations. (See Doughty, M. J. Consideration of Three Types of Spontaneous Eyeblink Activity in Normal Humans: during Reading and Video Display Terminal Use, in Primary Gaze, and while in Conversation. Optometry and Vision Science 78, 10 (2001), 712-725 and Skotte, J. H., Nojgaard, J. K., Jorgensen, L. V., Christensen, K. B., and Sjøgaard, G. Eye blink frequency during different computer tasks quantified by electrooculography. European journal of applied physiology 99, 2 (January 2007), 113-9, both of which are incorporated by reference herein.

TABLE 1

| Type of Task | Blinks per minute |
| --- | --- |
| Reading | 1.4-14.4 |
| Primary Gaze | 8.0-21.0 |
| Conversation | 10.5-32.5 |
| Active Visual Tasks | Avg. 5 |
| Passive Visual Tasks | Avg. 15 |

In another example, such threshold value or value range can represent a normal or adequate blink rate based on an interblink interval ("IBI") between blinks that is associated with an adequate tear film protection of the eyes (e.g., an OPI value of 1.0 or greater) as dictated by the ocular protection index ("OPI"). The OPI represents the relationship between the IBI and a tear film breakup time ("TFBUT") and can be represented by the formula OPI=TFBUT/IBI.

In general, a protected or non-dry eye surface of an eye can exist when the TFBUT is equal to or exceeds the IBI, and an unprotected or dry eye surface can exist when the TFBUT is less than the IBI. As such, if the OPI of the patient or user, such as determined by a healthcare provider is less than 1.0, the patient or user can be considered to be at risk for unprotected or inadequately protected ocular surface, which may cause symptoms associated with dry eye syndrome.

In some examples, such a threshold value can be about 5.97 seconds, which can be a mean or average IBI generally known to be associated with a blink rate not indicative of dry eye syndrome. In another example, such a threshold value can be a value of about 2.56 or about 3.05 seconds, which can be a mean or average IBI generally known to be associated with a blink rate indicative of dry eye syndrome (See Johnston P R, Rodriguez J, Lane K J, Ousler G, Abelson M B. The interblink interval in normal and dry eye subjects. Clin Ophthalmol. 2013; 7: 253-59, the contents of which are hereby incorporated by reference herein).

In response to the stored or recorded blink data relative to the normal or adequate blink rate, the controller can, such as automatically, or manually, via one or more user inputs to the controller via the user interface 119 or other input devices, vary parameters associated with the temporary appearance of the optical obstruction. For example, the number and/or the frequency of, transitions from the first state to the second state and the second state back to the first state (e.g., hazing events or appearance of the temporary optical obstruction) over a time interval or a predetermined period of time can be increased or decreased, such as further discussed below.

The response to the stored or recorded blink data by the processor or processing device (e.g., the controller) can vary in a number of ways. For example, in one example method, upon detection of a blink by the controller via the sensor data from the sensors 110 or the sensor 112, one or both of the lenses 102 or the screen 116 may be abruptly or gradually cleared of the optical obstruction or haze (e.g., transitioned or adjusted from the second state to the first state) over a predetermined period of time.

For example, the haze or optical obstruction can be quickly or slowly removed from the lenses 102 or the screen 116 (e.g., adjust the lenses 102 or the screen 116 from a second state to a first state) by the controller over a period of, for example, but not limited to, a time period of about, but not limited to, 1 or less than 1, 2, 3, 4, 5, 6, 7, 8, 9, 10, 11, 12, 13, 14, 15, 16, 17, 18, 19, 20, 21, 22, 23, 24, or 25 seconds, such as, but not limited to, after the controller determines that the user has blinked (i.e., either from both lenses if both eyes blinked or from a single one of the lenses 102 if only one eye blinked) from the sensor data.

Similarly, the haze or optical obstruction can be quickly or slowly created in the lenses 102 or the screen 116 by the controller over a period of, for example, but not limited to, 1 or less than 1, 2, 3, 4, 5, 6, 7, 8, 9, 10, 11, 12, 13, 14, 15, 16, 17, 18, 19, 20, 21, 22, 23, 24, or 25 seconds. In one such example, the controller can track elapsed time upon a detection of a blink using the sensor data from the sensors 110 or the sensor 112; and, a predetermined period or amount of time or a predetermined time interval has elapsed, the controller can cause the optical obstruction or haze to return quickly, such as instantaneously or within about one second, or more slowly, such as over about two or more seconds. In some examples, such a time period or interval can be sufficient or otherwise suitable to trigger or induce the blink in the patient or user, such as in examples configured to increase or help maintain an increased blink rate in the patient or user.

Further, the time period or interval over which the optical obstruction is created (e.g., increasing the haze) and the predetermined time period or interval over which the optical obstruction is removed (e.g., decreasing the haze) can be similar or different. In one such example, the time period or interval over which the optical obstruction is created and the time period or interval over which the optical obstruction is removed can be equal, such as, but not limited to, measuring about one second each. In another such example, the time period or interval over which the optical obstruction is created and the time period or interval over which the optical obstruction is removed can be unequal, such as, but not limited to, measuring about one second during creation of the optical obstruction and about 0.1 seconds during removal of the optical obstruction.

In some examples, the time period over which the haze or optical obstruction is removed can be determined by a detection of a blink by the controller. For example, the level of haze or optical obstruction may be relatively slowly increased by the controller (i.e., the percentage of light transmittance reduction through the lenses 102 or the screen 116 can be slowly increased) until a blink is detected, at which point the controller can immediately or quickly remove the optical obstruction or haze to immediately or quickly return the lenses 102 or the screen 116 to a clear or transparent state.

Any of the controllers or control systems discussed in the present disclosure can be configured or adapted to control or perform any of the operations discussed in this document via signal communication between the sensors 110 or the sensor 112 and the device or devices used for creating the optical obstruction or haze (e.g., lenses 102 or the screen 116). For example, in one example method or process of operation for triggering a blink response in a user or patient, the controller can generate (e.g., apply or send) a first signal (e.g., a voltage signal or the elimination of a voltage signal) to the first lens 102A, the second lens 102B, or the screen 116, to cause the lenses 102 or the screen 116 to transition (e.g., be adjusted) from the first state into the second state over a period of time to thereby trigger a blink reaction or response in the patient or user.

In an alternative example, such as in an example where the controller is realized in the form of onboard circuitry of the sensors 110 or the sensor 112, the sensors 110 or the sensor 112 can send or apply (e.g., generate) a first signal (e.g., a voltage signal or the elimination of a voltage signal) to, in turn, adjust first lens 102A, the second lens 102B, or the screen 116 to the second state.

Next, in some examples, the controller can intermittently or continuously monitor or analyze the sensor data from the sensors 110 or the sensor 112 to determine, confirm, or otherwise verify, that the adjustment of the first lens 102A, the second lens 102B, or the screen 116 to the second state, over a predetermined time period, has caused, or resulted in, a blink by the patient or user. In some examples, such as in an example where one or more components of the controller is realized in the form of onboard circuitry, the sensors 110 or the sensor 112 can apply or send (e.g., generate) a blink verification signal or blink confirmation signal to the processor of the controller upon detection of a blink in the user or patient.

Subsequently, after the controller has either received the blink verification signal, or has analyzed the sensor data independently of the sensors 110 or the sensor 112 to determine whether a blink has occurred in response to the first signal, the controller can begin to track elapsed time until a predetermined time interval has elapsed. Such a time interval can be, for example, but is not limited to, about 0.1, 0.2, 0.3, 0.4, 0.5, 0.6, 0.7, 0.8, 0.9, 1, 2, 3, 4, 5, 6, 7, 8, 9, or 10 seconds. This time interval can be based on any of the factors or parameters discussed in this disclosure with respect to a blink rate or an interblink interval (IBI), such as, for example, a desired blink rate selected or prescribed by a healthcare provide to help reduce the symptoms of dry eye syndrome, or a blink rate selected to increase a blink rate only during certain activities, such as electronic screen usage including viewing a monitor, television, or distant object.

Once the controller has determined that such a time interval has elapsed, the controller can apply or send a second signal (e.g., an elimination of a voltage signal or a voltage signal) to the first lens 102A, the second lens 102B, or the screen 116, to cause the lenses 102 or the screen 116 to transition (e.g., be adjusted) from the second state to the first over a predetermined period of time. In view of the above, the controller, together with the sensors 110 or the sensors 112, can collectively form a closed loop control and feedback system capable of verifying or otherwise confirming that each appearance of a temporary optical obstruction in the lenses 102 or the screen 116 has succeeded in triggering a blink in the user or patient, and proceeding to initiate another blink response based thereon (e.g., after a time period beginning upon verification of a blink, or a desired interblink interval) has elapsed.

As previously discussed above, the sensors 110 can, in some examples, be fixed to or embedded in the pair of eyeglasses 100 may be a video camera or an optical sensor. In some such examples, an optical sensor can include an infrared camera, or contact electrodes, such as those adapted for measuring electrooculography ("EOG"). Electrooculography measures the corneo-retinal standing potential that exists between the front and the back of the human eye, which is referred to as an electrooculogram. To measure this eye movement, pairs of electrodes can be placed either above and below the eye, or to the left and right of the eye, which may or may not be included in the frame 108 of the pair of eyeglasses 100.

If the eye moves or deviates from an on-center position toward one of the two electrodes, this electrode "sees" the positive side of the retina and the opposite electrode "sees" the negative side of the retina. Consequently, a potential difference can occur between the electrodes. Assuming that the resting potential is constant, the recorded potential may indicate a measure or value associated with the eye's position. Such electrodes may be connected in wired or wireless fashion to the controller, such as located in the pair of eyeglasses 100 or elsewhere.

Hence, one example configuration of a device or system for triggering a blink response in accordance with the present disclosure may include the pair of eyeglasses 100 and the sensors 110 can include contact sensors (e.g., EOG electrodes) that are configured to measure or determine a blink or blink event of the wearer, such as via blink or associated electrical pulse, of the pair of eyeglasses 100 and then remove a haze or optical obstruction from the lenses 102 thereof after the blink event or pulse has occurred.

The voltage pulses generated by the video camera or optical sensor of the sensors 110 may require signal conditioning to standardize the amplitude and timing before further processing, such by a processor of the controller. Various methods can be utilized to achieve the desired signal conditioning, such as both for adjusting voltage levels and converting the blink pulses into a uniform width. Potential techniques to amplify the pulse voltage amplitude may include, but are not limited to, transistor-based amplifier circuits designed with appropriate or otherwise suitable gain feedback, as well as transformers capable of stepping up lower AC voltages through magnetic induction. Standardizing the pulse widths may be accomplished using, but not limited to, monostable multivibrator circuits that output a fixed pulse width triggered by the input blink pulse.

In some examples, a dedicated timer integrated circuit, such as a 555 integrated circuit timer or other integrated circuit chips for timing applications, can also be configured in a monostable mode to achieve the desired fixed pulse width. Another example may include the use of a programmable microcontroller, such as an Arduino or a Raspberry Pi Pico microcontroller, running firmware designed to measure the input pulse width and generate corresponding output pulses of normalized timing. In such examples, the conditioned voltage pulse will be then adjusted to or based on the lenses 102 of the pair of eyeglasses 100 to remove the haze or optical obstruction in a desired manner, such as over a desired period of time after a blink has been determined or verified.

As previously discussed above, the sensors 110 can, in some examples, be fixed to or embedded in the pair of eyeglasses 100 may be a video camera or an optical sensor. In some such examples, an optical sensor can include an infrared camera, or contact electrodes, such as those adapted for measuring electrooculography ("EOG"). Electrooculography measures the corneo-retinal standing potential that exists between the front and the back of the human eye, which is referred to as an electrooculogram. To measure this eye movement, pairs of electrodes can be placed either above and below the eye, or to the left and right of the eye, which may or may not be included in the frame 108 of the pair of eyeglasses 100.

If the eye moves or deviates from an on-center position toward one of the two electrodes, this electrode "sees" the positive side of the retina and the opposite electrode "sees" the negative side of the retina. Consequently, a potential difference can occur between the electrodes. Assuming that the resting potential is constant, the recorded potential may indicate a measure or value associated with the eye's position. Such electrodes may be connected in wired or wireless fashion to the controller, such as located in the pair of eyeglasses 100 or elsewhere.

Hence, one example configuration of a device or system for triggering a blink response in accordance with the present disclosure may include the pair of eyeglasses 100 and the sensors 110 can include contact sensors (e.g., EOG electrodes) that are configured to measure or determine a blink or blink event of the wearer, such as via blink or associated electrical pulse, of the pair of eyeglasses 100 and then remove a haze or optical obstruction from the lenses 102 thereof after the blink event or pulse has occurred.

The voltage pulses generated by the video camera or optical sensor of the sensors 110 may require signal conditioning to standardize the amplitude and timing before further processing, such by a processor of the controller. Various methods can be utilized to achieve the desired signal conditioning, such as both for adjusting voltage levels and converting the blink pulses into a uniform width. Potential techniques to amplify the pulse voltage amplitude may include, but are not limited to, transistor-based amplifier circuits designed with appropriate or otherwise suitable gain feedback, as well as transformers capable of stepping up lower AC voltages through magnetic induction. Standardizing the pulse widths may be accomplished using, but not limited to, monostable multivibrator circuits that output a fixed pulse width triggered by the input blink pulse.

In some examples, a dedicated timer integrated circuit, such as a 555 integrated circuit timer or other integrated circuit chips for timing applications, can also be configured in a monostable mode to achieve the desired fixed pulse width. Another example may include the use of a programmable microcontroller, such as an Arduino or a Raspberry Pi Pico microcontroller, running firmware designed to measure the input pulse width and generate corresponding output pulses of normalized timing. In such examples, the conditioned voltage pulse will be then adjusted to or based on the lenses 102 of the pair of eyeglasses 100 to remove the haze or optical obstruction in a desired manner, such as over a desired period of time after a blink has been determined or verified.

In some examples, the sensors 110 or the sensor 112 can include an ambient humidity sensor, which can communicate humidity values to the controller. In such examples, the controller may determine, via signal communication with the humidity sensor, that in relatively dry environments, a higher frequency of blinking should occur. In response, the therefore may increase the rate of causing hazing events (e.g., reduce the time interval between a first signal and a second signal, or otherwise between the lenses 102 or the screen 116 transition from the first state to the state and back to the first state from the second state to cause a blink). See Tabernero, Juan & Garcia-Porta, Nery & Artal, Pablo & Pardhan, Shahina. (2021). Intraocular Scattering, Blinking Rate, and Tear Film Osmolarity After Exposure to Environmental Stress. Translational vision science & technology. 10. 12. 10.1167/tvst.10.9.12, the contents of which are hereby incorporated by reference herein).

In view of all the above, various parameters associated with the creation or removal of an optical obstruction in front of a user, such as a frequency of the temporary optical obstruction (e.g., a time interval or period between two consecutive appearances of the second state or haze effect in the lenses 102 or the screen 116), the length of each appearance of the optical obstruction (e.g., how long the lenses 102 or the screen 116 are maintained in the second state), or the amount of light transmission during the appearance of the optical obstruction (e.g., the percentage of light transmittance reduction in the second state) may be determined and/or changed to better match recommended or desired blinking needs various environments or during various activities.

Figure 10:
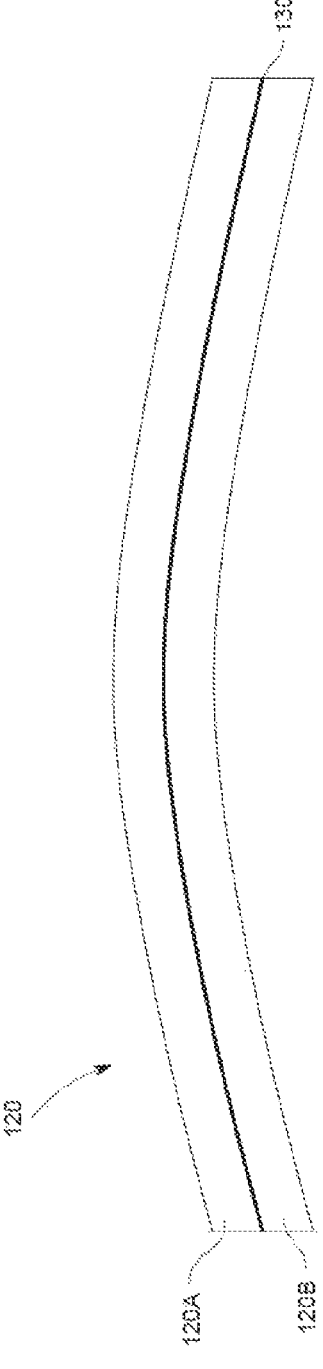
FIG. 10 is a side view of a lens stack including an electrodynamic layer in accordance with an example embodiment.

FIG. 10 illustrates a lens stack 120 including an electrodynamic layer 130. The lens stack 120 can be generally representative of, or can include, one, or all, of a plurality of individual layers forming or otherwise comprising the first lens 102A, the second lens 102B, the screen 116. The lenses 102, or the lens stack 120, can each include various numbers of individual layers, such as, but not limited to, two, three, four, five, six, seven, eight, nine, or ten individual layers.

In some examples, the lens stack 120 can include a first layer 120A and a second layer 120B. In one example, one, or both, of the first layer 120A and the second layer 120B can represent a single polycarbonate layer. In other examples, the first layer 120A or the second layer 120B can each be made from various other materials, such as including, but not limited to, glass or glasses laminates, nylon or nylon laminates, a polyimide laminate, a polyethylene terephthalate ("PET") laminate or biaxially oriented PET triacetate laminate, or a non-polarized or polarized sheet laminate.

The lens stack 120 can include the electrodynamic layer 130. The electrodynamic layer 130 can be representative of the haze-inducing layer 106 shown in, and discussed with reference to, FIGS. 1-2 above. The electrodynamic layer 130 can thereby represent one or more layers of the lenses 102 or the lens stack 120 that is configured to, or is otherwise capable of, adjusting or transitioning the lenses 102 between the first state shown in FIG. 1 and the second state shown in FIG. 2 when voltage is applied, or if a voltage applied thereto is eliminated or no longer applied.

In some examples, the electrodynamic layer 130 can be positioned on, or located between, the first layer 120A and the second layer 120B. In other examples, the electrodynamic layer 130 can be located on, or between, various other layers of the lenses 102 or the lens stack 120. In one alternative example, the electrodynamic layer 130 can be positioned on an outer facing, or otherwise outermost, surface of the first layer 120A or the second layer 120B.

The electrodynamic layer 130 can be made from one or more layers of various materials. For example, the electrodynamic layer 130 can be made from, but not limited to, a variety of laminates including a liquid crystal film or layer embedded therein, such as any of a polyethylene terephthalate ("PET") laminate, a polycarbonate laminate, a nylon laminate, a polyimide laminate, a biaxially oriented PET triacetate laminate, or a non-polarized or polarized sheet laminate. In various examples, such a liquid crystal film or layer can be a polymer-dispersed liquid crystal film ("PDLC") layer. In one specific example, the liquid crystal laminate (e.g., the electrodynamic layer 130) can be a PET laminate containing a polymer-dispersed liquid crystal film (PDLC) layer, including polymer-dispersed liquid crystal films having high clearing points, enabling higher temperature processes.

In some examples, the lens stack 120 or the electrodynamic layer 130 (e.g., the liquid crystal laminate) can be formed, or integrated, into the lenses 102 via an injection molding process. In one such example, the lens stack 120 can include a liquid crystal laminate (e.g., the electrodynamic layer 130) molded between two or more polycarbonate films or layers with a thermally, ultraviolet light, or electron-beam curable optical glue or pressure sensitive adhesive. In one specific example, the lens stack 120 can include a liquid crystal PDLC layer, which can be the electrodynamic layer 130, laminated between two polycarbonate sheets each about 12 millimeters in thickness, which, in some examples, can represent the first layer 120A and the second layer 120B, using an optically clear and pressure sensitive adhesive, and/or a thermally cured polyurethane adhesive, one example of which may be a 3M 8213 OCA adhesive curable at about eighty degrees Fahrenheit. Other non-limiting examples of pressure-sensitive adhesives include 3M 8146-2 OCA and 3M CEF 3104AS OCA.

In another specific example, the electrodynamic layer 130 can be an infrared liquid crystal (IRLC) film, or a suspended particle device (SPD) film, each of which are types of PDLC film with relatively high clearing points to therefore increase heat resistance. This can be helpful when the lens stack 120 or the electrodynamic layer 130 are molded or are otherwise exposed to significant levels of heat. In some examples, the electrodynamic layer 130, the first layer 120A, the second layer 120B, or other layers of the lens stack 120, may have a variety of colors, such as including white, gray, brown, or others. Moreover, in some examples, the electrodynamic layer 130 can change colors between the first state and the second state, such as by transitioning to grey from white or dark brown from light brown.

Figure 8:
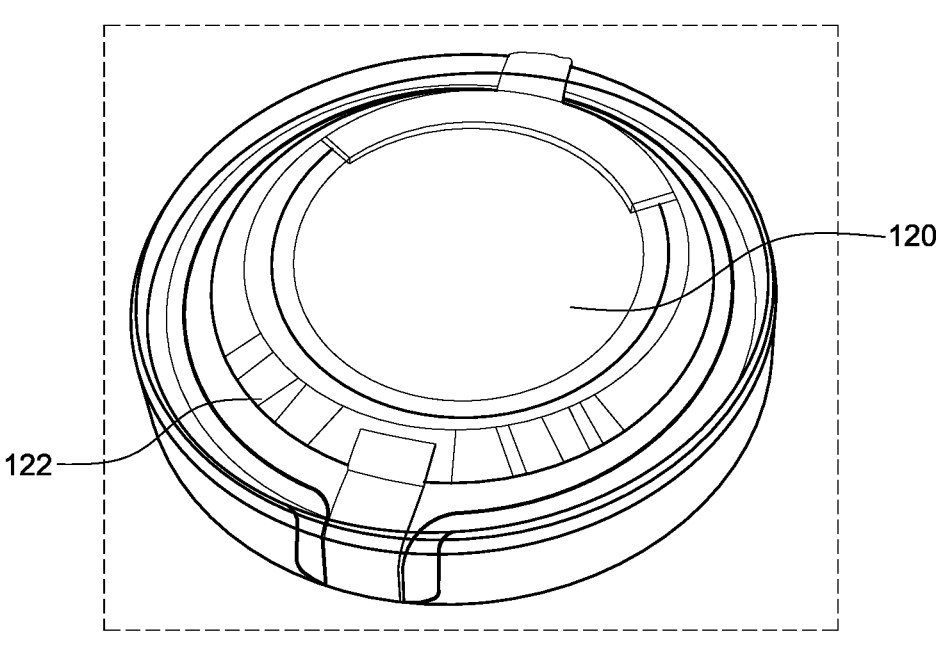
FIG. 8 illustrates an upper perspective view of the lens stack of FIG. 7 after it has been injection molded into a desired lens shape in accordance with an example embodiment.

In some examples, after lamination of various components or layers to create the lens stack 120, the lens stack 120 may be directly molded into a polycarbonate or other material of lens, which can, in some examples, represent the lenses 102 of the pair of eyeglasses 100, without undergoing a forming process, such as shown in FIG. 8. In such an example, the lens stack 120 can be placed directly into a lens mold after it has been created or otherwise made through lamination, and then molded into a complete lens (e.g., the first lens 102A or the second lens 102B) by laminating the lens stack 120 between, or casting the lens stack 120 into or within, polycarbonate or other materials introducing into the lens mold. This can help to avoid damage to the electrodynamic layer 130 or a liquid crystal layer within the lens stack 120 by avoiding shaping of the lens stack 120.

In an example, the electrodynamic layer 130, such as a liquid crystal laminate device or water, may be made with PET and laminated with polycarbonate sheets (e.g., 12 mil polycarbonate sheets) with optically clear pressure sensitive adhesives. The use of such adhesives may allow the polycarbonate to adhere to the injection molding polycarbonate materials. The polycarbonate laminates may be molded with or without forming. Some of the laminates may be formed to a 0-base, 2-base and/or 4-base curve by application of heat, vacuum, and forming mold after masking with high temperature masks.

Figure 7:
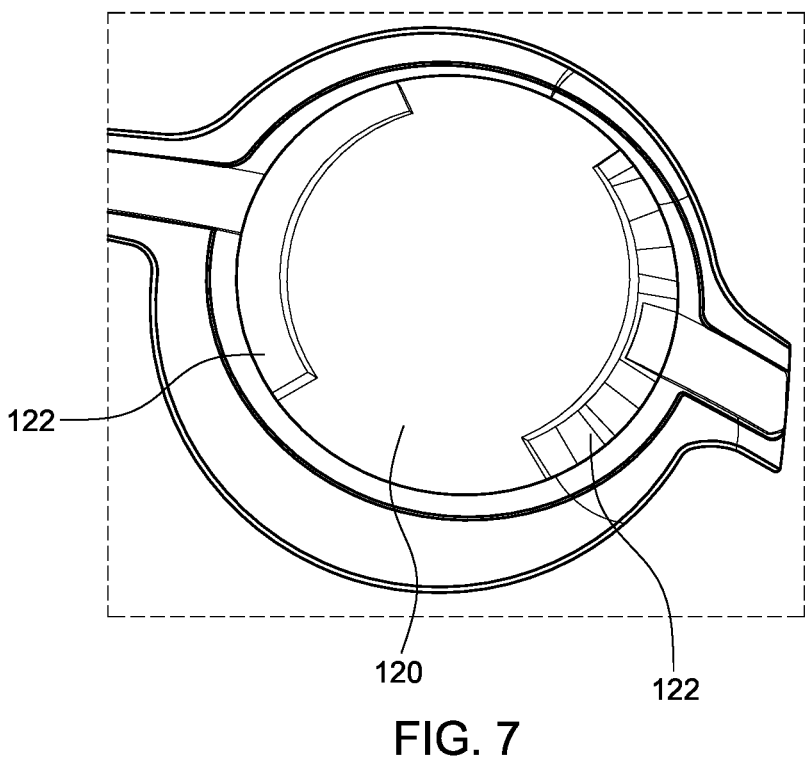
FIG. 7 illustrates a top perspective view of a formed lens that is composed of at least two electrical contacts that are configured to supply power to a lens stack in accordance with an example embodiment.

In other examples, after lamination of various components or layers to create the lens stack 120, the lens stack 120 may first be formed before undergoing final molding into a finished or completed polycarbonate, or other material, of lens, such as via the application of heat and pressure, to give a permanent curvature to the lens stack 120, such as shown in FIG. 7. Such a permanent curvature can be, for example, a base curve or curvature (indicated by a positive or negative number) selected or configured to impart a corrective power to the lens stack 120, such as created by the application of a vacuum to the lens stack 120 in a forming mold after the lens stack 120 heated, such as with a relatively high temperature mask.

In some such examples, forming of the lens stack 120 before molding, such as to impart a corrective curvature thereto, may not significantly affect the performance of, or otherwise damage, the electrodynamic layer 130 or other liquid crystal layers located within the lens stack 120. For example, FIG. 11 illustrates a graph showing response times of the electrodynamic layer 130 before and after forming and molding of the lens stack 120 in response to the application of voltage thereto, and FIG. 12 illustrates a table showing response times of the electrodynamic layer 130 before and after forming and molding of the lens stack 120 in response to the application of voltage thereto.

Figure 11:
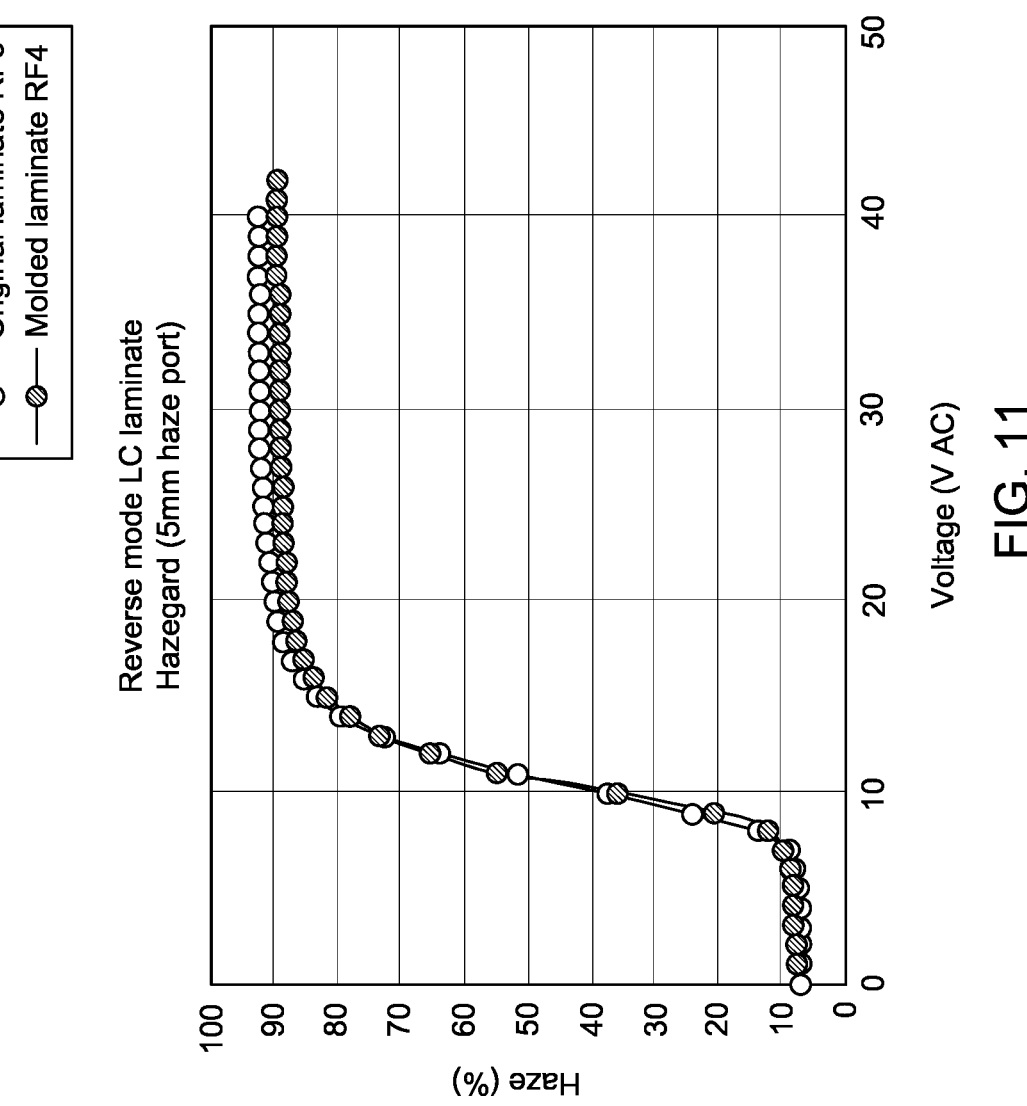
FIG. 11 is a graph showing response times of an electro-dynamic layer before and after molding of a lens stack, in accordance with an example embodiment.

More particularly, before the performance results (e.g., the response times) shown in FIGS. 11-12 were obtained, the lens stack 120 and the electrodynamic layer 130 tested was first formed into a four base curve shape. While a four base curve can represent a significant amount of curvature that is usable for a wide range of corrective lenses, it is to be appreciated that forming and molding of the lens stack 120 and the electrodynamic layer 130 thereof is not so limited, and such curvatures for imparting a corrective power of the lens stack 120 may not significantly or otherwise appreciably vary or affect the response of the electrodynamic layer 130 in the operation of various embodiments of the present disclosure.

Various types of laminates may be utilized. As an example, an "RF" laminate as referenced in FIGS. 12-14 may comprise a reverse phase polymer dispersed liquid crystal laminate which is clear at 0 volts. A "PF" laminate may comprise a polymer dispersed liquid crystal laminate having a maximum haze at 0 volts and which is clear at 40 volts. A "G" laminate may comprise a polymer dispersed liquid crystal laminate with maximum haze at 0 volts and which is clear at 70 volts AC. Other types of laminates may be dark at 0 volts and clear at 100 volts AC. It thus should be appreciated that the "trigger conditions" of various laminates may vary in different embodiments, with some laminates being clear at null voltage and other laminates being clear at relatively higher voltages. Such laminates have shown efficacy at a range of different base curves (e.g., 0B, 2B, 4B) and with different types of adhesives (e.g., pressure sensitive adhesives, moisture cured adhesives, and the like).

Figure 13:
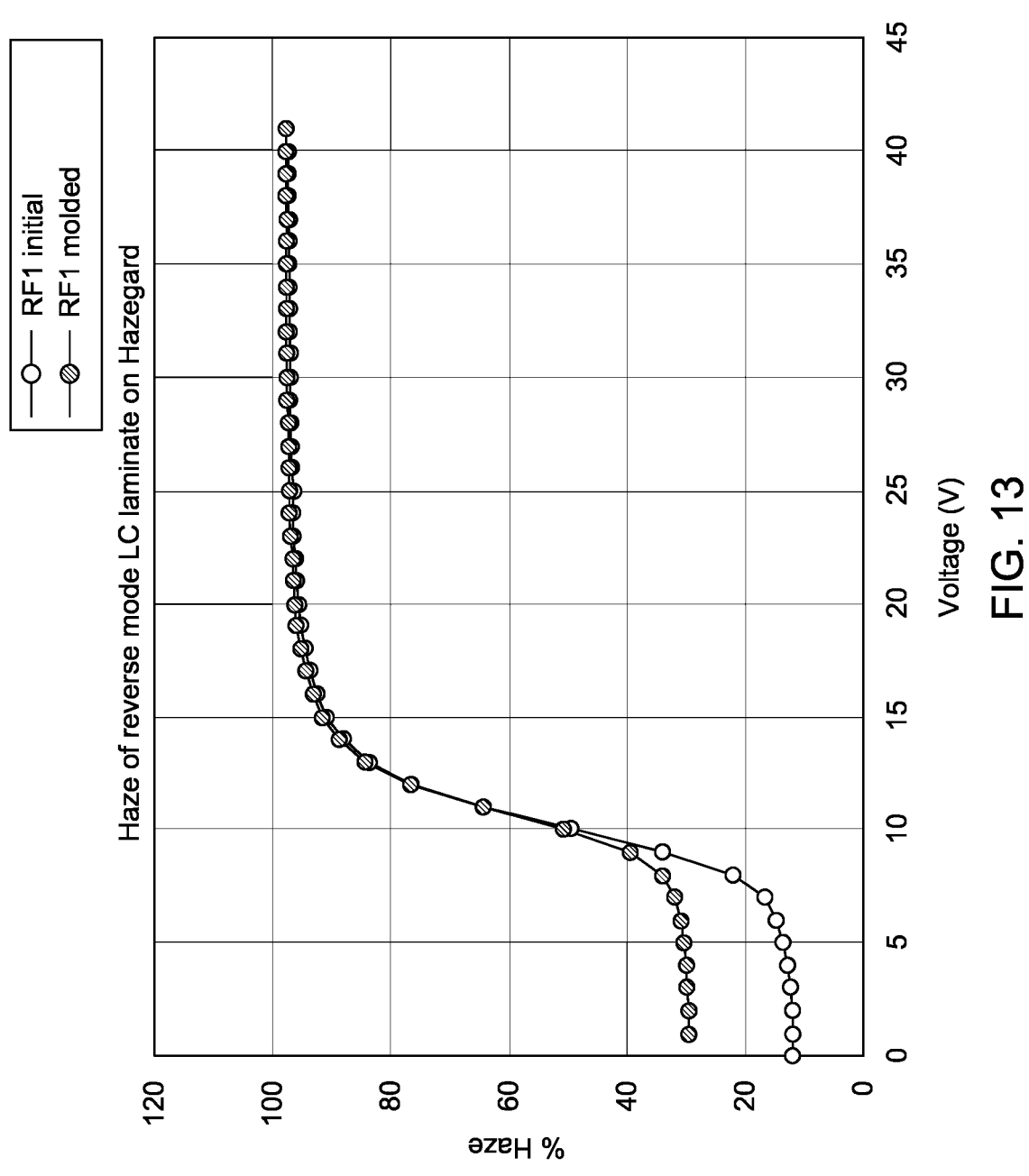
FIG. 13 is a graph showing response times of laminates made with moisture cured adhesive before and after molding of a lens stack, in accordance with an example embodiment.

In some examples, liquid crystal devices may be laminated with polycarbonate sheets (e.g., 12 mil polycarbonate sheets) with moisture cured adhesives. The curing process may involve exposure of the laminates to elevated temperature for an extended period of time. The laminates may be molded subsequently with or without forming. FIG. 13 is a graph illustrating haze of liquid crystal laminates before and after injection molding, with the laminates having been made with moisture cured adhesive. FIG. 14 is a table illustrating response time before and after injection molding, with the laminates having been made with moisture cured adhesive. An example moisture cured adhesive may comprise an adhesive based on polyurethane chemistry. As is evident from the preceding figures, significant deterioration of the haze or optical obstruction of the liquid crystal film was not observed after injection molding.

In view of the above, it is to be appreciated that the lens stack 120, such as including the first layer 120A, the second layer 120B, and the electrodynamic layer 130, can be formed to impart any corrective power (e.g., be a corrective power lens) thereto. Moreover, other layers of the lenses 102, such as encompassing or surrounding the lens stack 120, can be formed to impart a corrective power during or after molding or casting, during which the lens stack 120 be incorporated thereinto. For example, the lenses 102, the first layer 120A, the second layer 120B, the electrodynamic layer 130, can be adapted, formed, or otherwise tailored or manufactured to accommodate a wide variety of eyeglass prescriptions, which can include, among others, power ("PWR"), which refers to a positive or a negative number indicating the degree of correction for improving near vision and/or distance vision, cylinder ("CYL"), which refers to a positive or negative number for addressing astigmatism, axis ("AX"), addition ("ADD"), single vision near ("SVN"), or single vision distance ("SVD").

In additional examples, the lens stack 120 or the electrodynamic layer 130, or any of the lenses 102 discussed above, can be embedded into cast lens materials during final casting using the casting process as described in U.S. Patent Publication No.: 2007/0122626, which is incorporated by reference; or can be attached to any surface of the lenses 102 or the lens stack 120 thereof via film glue. Such a casting process can include introducing a liquid polycarbonate material into an ophthalmic lens glass mold containing the lens stack 120 therein.

Figure 6:
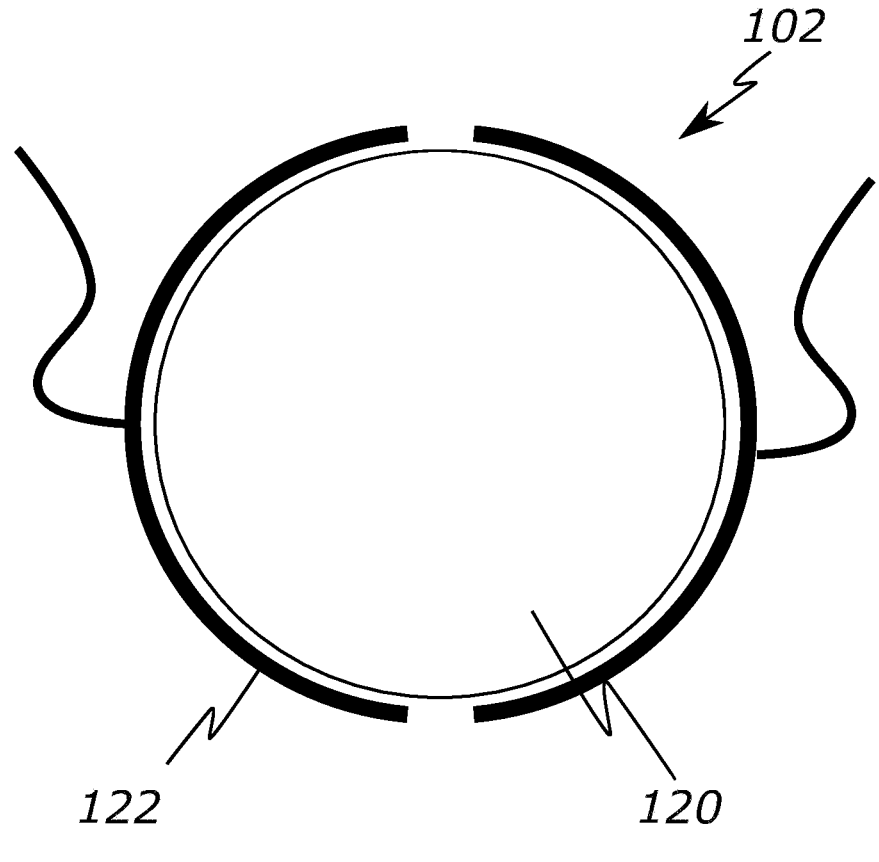
FIG. 6 illustrates a lens that is composed of at least two electrical contacts or connections that are configured to supply power to a lens stack in accordance with an example embodiment.

FIG. 6 illustrates an example lens stack 120 including at least two electrical contacts 122. FIGS. 7-8 also illustrate examples of the lens stack 120. The at least two electrical contacts 122 are discussed with reference to FIGS. 6-8 below concurrently. The at least two electrical contacts 122 can generally any electrical connection or contact points in conductive or electrical communication with the electrodynamic layer 130 or the haze-inducing layer 106. In some examples, the screen 116 (FIG. 5) can also include the at least two electrical contacts 122.

The least two electrical contacts 122 can be electrically connected to, or otherwise in electrical or conductive communication with, any controller discussed in this document. The at least two electrical contacts 122 can be thereby be configured to receive and apply voltage to, the electrodynamic layer 130 located within the lens stack 120 or the screen 116 to enable the controller control or modulate the appearance of the haze or optical obstruction (e.g., adjust the lenses 102 or the screen 116 from the first state to the second state or adjust the lenses 102 or the screen 116 from the second state to the first state.

In one specific example, the least two electrical contacts 122 can be positioned within a PDLC film or layer, such as of the lens stack 120 or the screen 116. For example, PDLC film or layer generally have or include sponge-like polymer network combined with liquid crystals, and the at least two electrical contacts 122 can represent opaque or transparent electrodes or electrode layers located on each side of the sponge-like polymer network adapted to induce current through the polymer network and the liquid crystals.

In some examples, when a voltage, current, or other electrical signal is applied to the electrodynamic layer 130 by the controller, the electrodynamic layer 130, such as of the lenses 102 or the screen 116 can become clear (e.g., adjust from the second state to the first state), and when the electrical signal is stopped, eliminated, or otherwise removed from the electrodynamic layer 130, the lenses 102 or the screen 116 can become hazy or opaque (e.g., adjust from the first state to the second state). In other examples, when a voltage, current, or other electrical signal is applied to the electrodynamic layer 130 by the controller, the electrodynamic layer 130, the lenses 102 or the screen 116 can become hazy or opaque (e.g., adjust from the first state to the second state), and when the electrical signal is stopped, eliminated, or otherwise removed from the electrodynamic layer 130 can become clear (e.g., adjust from the second state to the first state.

Figure 9:
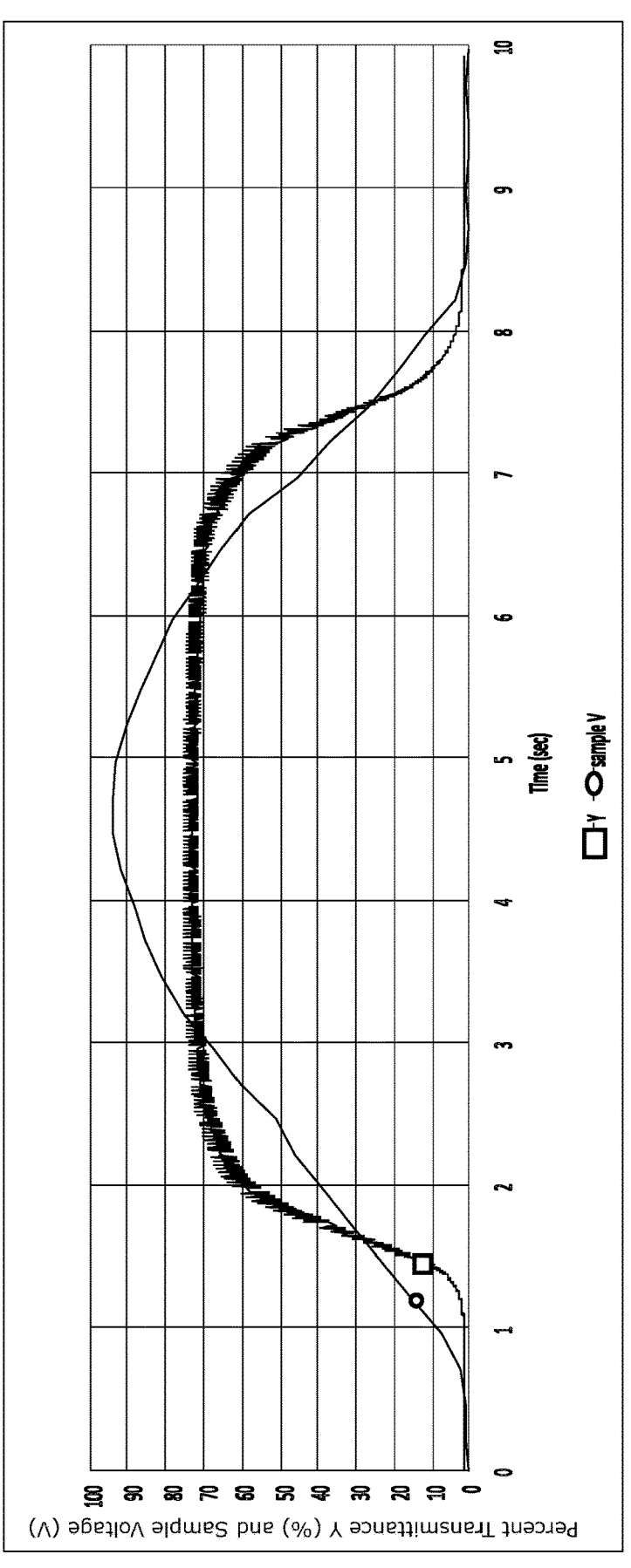
FIG. 9 is a graph illustrating how a lens stack may be controlled to reach a specific amount of haze at or around a specific amount of time in accordance with an example embodiment.

FIG. 9 illustrates a graph illustrating adjustment of an electrodynamic layer between a first state and a second state over a period of time using a voltage. As shown in FIG. 9, the electrodynamic layer 130 (e.g., the haze-inducing layer 106) of the lens stack 120 or the screen 116, may be controlled, such as via any controller discussed in the present disclosure, using various means or methods described above or below. For example, the electrodynamic layer 130 can be modulated, actuated, activated, or otherwise controlled to reach the second state (e.g., a reduced amount of limited light transmittance through the lenses 102 or the screen 116) at or around a specific amount of time based on the parameters of the voltage applied thereto.

In some examples, the controller can be configured to gradually increase the voltage (e.g., the first signal) applied to the optical obstructive feature (e.g., the electrodynamic layer 130 of the lenses 102) over various time intervals of periods of time, such as discussed above with reference to FIGS. 4-5, until a predetermined level of voltage is reached. In such examples, the predetermined level of voltage can dictate, determined, or otherwise correspond to, the second state (e.g., a percentage of light transmittance reduction through the lenses 102 or the screen). As can be appreciated, the percentage of light transmittance reduction at the predetermined voltage level, or any particular voltage, can vary depending on one or materials of the electrodynamic layer 130, such as a type of liquid crystal laminate present in the electrodynamic layer 130.

In some examples, alternating current ("AC") power may be used by the controller (e.g., applied to the at least two electrical contacts 122) to control or modulate (e.g., adjust) the electrodynamic layer 130 between the first state and the second state. In other examples, direct current ("DC") power may be used by the controller (e.g., applied to the at least two electrical contacts 122) to control or modulate (e.g., adjust) the electrodynamic layer 130 between the first state the second state. In an example where DC power is used, DC voltage can be applied by the controller with pulsing and frequency modulation to achieve the second state (e.g., a desired level of haze) within a desired amount of time, such as any of the time periods or intervals discussed above.

In view of all the above, any of the devices or systems of the present specification may be used to treat various vision related conditions that may be addressed by increasing a blink rate of a user, such as including dry eye syndrome. Further, any of the devices or systems of the present specification may be used to treat Amblyopia. For example, a clinician, physician, optometrist, or other healthcare professional may first determine a dominant, favored, or otherwise "good" eye that properly tracks a desired vision target, and also determine a less dominant, less favored, "lazy" eye. Any of the haze-creating or inducing devices may then be modulated or controlled to create and maintain a haze in front of the dominant eye while allowing clear vision in front of the less dominant eye for a period of time (e.g., hours, days, weeks, or longer).

This treatment may be especially helpful when using the pair of eyeglasses 100, though other described devices are also possible. In this way, the amount of haze (e.g., the percentage of light transmittance reduction in the second state) needed for Amblyopia is determined by the prescribing physician. Optionally, the pair of eyeglasses 100 may include the previously described sensors 110 which may take the form of one or more cameras facing the user's eyes. These cameras may monitor the movements of the user's less dominant eye and optionally the more dominant eye to track improvement. For example, the camera may monitor the eye and store eye position data for one or both eyes to determine if both eyes are better tracking together or if the movements of the less dominant eye improve to a more normal movement pattern.

In any of the above examples of embodiments, a method of use of a device or system for triggering a blink response can include monitoring an eye for one or more blinks over a predetermined period of time, determining that fewer than a predetermined number of blinks have occurred during the predetermined period of time, modulating haze on a hazing device in front of the eye (e.g., eyeglasses or screen) to generate a blink, and removing the haze from the device. The causing of haze may further include applying voltage to a liquid crystal laminate (or similar display) on the device for a predetermined period of time.

While the terms "haze", "hazy" or "optical obstruction" are generally used herein, it is to be appreciated that this term can also mean shading, darkening, or otherwise adjusting the transmittance or a focus of light through an optical element. Further, while the term "the controller" is generally used herein with reference to various examples, it is to be appreciated that this term can include a control system or control unit including any of microprocessor, microcontroller, processing device, computer or computing device, a power supply such as an electrical transformer or battery, and various other methods, systems, and/or devices for establishing communication between the electrodynamic layer 130, the haze-inducing layer 106, the screen 116, or any other device for creating a temporary optical obstruction in front of a patient or user using voltage.

Additionally, while a number of examples of the devices and system for trigger blink response in a patient or may utilize closed loop control based on sensor feedback to determine whether the data is above or below certain thresholds and then either increase or decrease the frequency of the induced blink response (either accounting for the user's actual blinks or without regard for the user's actual blinks (if no eye tracking sensor is present), it is to be appreciated that, in other examples, the frequency of the induced blink response can be varied without regard for the user's actual blinks if no eye tracking sensor is present, such as in response to one or more user inputs to a user interface.

The following, non-limiting examples, detail certain aspects of the present subject matter to solve the challenges and provide the benefits discussed herein, among others.

Example 1 is a device for inducing a blink response in a user, comprising: creating a haze for a predetermined amount of time in front of one or more eyes of the user.

In Example 2, the subject matter of Example 1 includes, wherein the device is eyeglasses.

In Example 3, the subject matter of Examples 1-2 includes, wherein the device is a screen in front of a monitor.

In Example 4, the subject matter of Examples 1-3 includes, wherein creating the haze includes changing a voltage applied to a PDLC layer.

In Example 5, the subject matter of Example 4 includes, wherein the device comprises a multi-layer film or substrate comprising polycarbonate and/or polyethylene terephthalate films and the PDLC layer is molded into a spherical or corrective prescription lens.

In Example 6, the subject matter of Examples 1-5 includes, sensors configured to monitor the user's eye for blinking.

In Example 7, the subject matter of Examples 1-6 includes, sensors configured to monitor depth of field, colors being viewed by the user, light intensity, rate of change of the user's visual stimulus, and/or ambient humidity around the user.

In Example 8, the subject matter of Examples 1-7 includes, wherein the time interval is about 0.1, 0.2, 0.3, 0.4, 0.5, 0.6, 0.7, 0.8, 0.9, 1, 2, 3, 4, 5, 6, 7, 8, 9, or 10 seconds.

In Example 9, the subject matter of Examples 1-8 includes, wherein a transmittance of the haze is adjusted based on ambient light around a user.

In Example 10, the subject matter of Examples 1-9 includes, wherein a transmittance of the haze is adjustable by the user via a computer or phone app.

In Example 11, the subject matter of Examples 1-10 includes, wherein the haze is removed based on whether the user have been detected to have blinked.

In Example 12, the subject matter of Examples 2-11 includes, wherein the eyeglasses include one or more sensors that detect blinking of one or more eyes of the wearer.

Example 13 is a device for triggering a blink response, comprising: a sensor configured to detect a blink in at least one eye; a lens including a plurality of layers, at least one of the plurality of layers comprising an electrodynamic layer in communication with the sensor; wherein the electrodynamic layer is configured to adjust the lens between a first state and a second state in response to a first signal by the sensor; and, wherein the electrodynamic layer is configured to adjust the lens between the second state and the first state in response to a second signal by the sensor.

In Example 14, the subject matter of Example 13 includes, wherein, in the first state, the lens is transparent or clear.

In Example 15, the subject matter of Example 14 includes, wherein, in the second state, the lens is at least partially obscured or obstructed.

In Example 16, the subject matter of Example 15 includes, wherein, in the second state, the lens is semi-transparent, semi-opaque, opaque, hazy, shaded, or blurred.

In Example 17, the subject matter of Examples 13-16 includes, wherein the plurality of layers comprises at least one polycarbonate layer.

In Example 18, the subject matter of Example 17 includes, wherein the at least one polycarbonate layer includes a first polycarbonate layer and a second polycarbonate layer, the electrodynamic layer being positioned between the first polycarbonate layer and the second polycarbonate layer.

In Example 19, the subject matter of Example 18 includes, wherein at least one of the first polycarbonate layer and the second polycarbonate comprises a corrective power.

In Example 20, the subject matter of Example 19 includes, wherein the electrodynamic layer is an injection molded polyethylene terephthalate laminate including a liquid crystal film.

In Example 21, the subject matter of Example 20 includes, wherein the electrodynamic layer includes at least two electrical contacts in electrical communication with the liquid crystal film.

In Example 22, the subject matter of Example 21 includes, wherein the sensor comprises a camera.

Example 23 is a system for triggering a blink response, comprising: a sensor configured to detect a blink in at least one eye; a lens including a plurality of layers, at least one of the plurality of layers comprising an electrodynamic layer in communication with the sensor; wherein the electrodynamic layer is configured to adjust a lens between a first state and a second state in response to a first signal; wherein the electrodynamic layer is configured to adjust the lens between the second state and the first state in response to a second signal; and a controller in communication with the sensor and the electrodynamic section of the lens, the controller being configured to generate the first signal and the second signal based on signal communication with the sensor.

In Example 24, the subject matter of Example 23 includes, wherein: in the first state, the lens is transparent or clear; and in the second state, the lens is at least partially obscured or obstructed.

In Example 25, the subject matter of Example 24 includes, wherein the second state is defined by a 10-30 percent reduction of light transmittance through the lens, a 31-50 percent reduction in light transmittance through the lens, or a 51-70 percent reduction in light transmittance through the lens.

In Example 26, the subject matter of Examples 24-25 includes, wherein: the controller is configured to generate the second signal upon receipt of a blink verification signal from the sensor; and the controller is configured to generate the first signal after a time interval has elapsed, the time interval beginning upon receipt of the blink verification signal by the controller.

In Example 27, the subject matter of Example 26 includes, wherein the time interval is about 0.1, 0.2, 0.3, 0.4, 0.5, 0.6, 0.7, 0.8, 0.9, 1, 2, 3, 4, 5, 6, 7, 8, 9, or 10 seconds.

In Example 28, the subject matter of Examples 26-27 includes, wherein the controller is adapted to vary the time interval based on at least one of: a predetermined threshold blink rate, ambient light intensity, colors being viewed through the lens, ambient humidity, a depth of field, or a rate of change of visual stimuli.

In Example 29, the subject matter of Example 28 includes, wherein the sensor comprises a camera and a humidity sensor.

In Example 30, the subject matter of Example 29 includes, a user interface in electrical communication with the controller, the user interface being adapted to enable a user to select the time interval between generation of the first signal and the second signal by the controller.

In Example 31, the subject matter of Example 30 includes, wherein the user interface is displayed on a desktop computer, an electronic tablet, or a mobile phone.

Example 32 is a method of inducing a blink response, the method comprising: adjusting an electrodynamic layer of a lens between a first state and a second state in response to a first signal by a sensor configured to detect a blink in at least one eye; and adjusting the lens between the second state and the first state in response to a second signal by the sensor.

Example 33 is at least one machine-readable medium including instructions that, when executed by processing circuitry, cause the processing circuitry to perform operations to implement of any of Examples 1-32.

Example 34 is an apparatus comprising means to implement of any of Examples 1-32.

Example 35 is a system to implement of any of Examples 1-32.

Example 36 is a method to implement of any of Examples 1-32.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device for triggering a blink response, comprising:
a sensor configured to detect a blink in at least one eye;
a lens including a plurality of layers, at least one of the plurality of layers comprising an electrodynamic layer in communication with the sensor;
wherein the electrodynamic layer is configured to adjust the lens from a first state to a second state in response to a first signal by the sensor; and,
wherein the electrodynamic layer is configured to adjust the lens from the second state to the first state in response to a second signal that is generated upon receipt of a blink verification by the sensor.

2. The device of claim 1, wherein, in the first state, the lens is transparent or clear.

3. The device of claim 2, wherein, in the second state, the lens is at least partially obscured or obstructed.

4. The device of claim 3, wherein, in the second state, the lens is semi-transparent, semi-opaque, opaque, hazy, shaded, or blurred.

5. The device of claim 1, wherein the plurality of layers comprises at least one polycarbonate layer.

6. The device of claim 5, wherein the at least one polycarbonate layer includes a first polycarbonate layer and a second polycarbonate layer, the electrodynamic layer being positioned between the first polycarbonate layer and the second polycarbonate layer.

7. The device of claim 6, wherein at least one of the first polycarbonate layer and the second polycarbonate comprises a corrective power.

8. The device of claim 7, wherein the electrodynamic layer is an injection molded polyethylene terephthalate laminate including a liquid crystal film.

9. The device of claim 8, wherein the electrodynamic layer includes at least two electrical contacts in electrical communication with the liquid crystal film.

10. The device of claim 9, wherein the sensor comprises a camera.

11. A system for triggering a blink response, comprising:
a sensor configured to detect a blink in at least one eye;
a lens including a plurality of layers, at least one of the plurality of layers comprising an electrodynamic layer in communication with the sensor;
wherein the electrodynamic layer is configured to adjust a lens between a first state and a second state in response to a first signal;

wherein the electrodynamic layer is configured to adjust the lens between the second state and the first state in response to a second signal; and a controller in communication with the sensor and the electrodynamic layer of the lens, the controller being configured to generate the first signal and the second signal based on signal communication with the sensor, and wherein the controller is configured to generate the second signal upon receipt of a blink verification signal from the sensor; and the controller is configured to generate the first signal after a time interval has elapsed, the time interval beginning upon receipt of the blink verification signal by the controller.

12. The system of claim 11, wherein:

in the first state, the lens is transparent or clear; and in the second state, the lens is at least partially obscured or obstructed.

13. The system of claim 12, wherein the second state is defined by a 10-30 percent reduction of light transmittance through the lens, a 31-50 percent reduction in light transmittance through the lens, or a 51-70 percent reduction in light transmittance through the lens.

14. The system of claim 11, wherein the time interval is about 0.1, 0.2, 0.3, 0.4, 0.5, 0.6, 0.7, 0.8, 0.9, 1, 2, 3, 4, 5, 6, 7, 8, 9, or 10 seconds.

15. The system of claim 11, wherein the controller is adapted to vary the time interval based on at least one of: a predetermined threshold blink rate, ambient light intensity, colors being viewed through the lens, ambient humidity, a depth of field, or a rate of change of visual stimuli.

16. The system of claim 15, wherein the sensor comprises a camera and a humidity sensor.

17. The system of claim 16, further comprising a user interface in electrical communication with the controller, the user interface being adapted to enable a user to select the time interval between generation of the first signal and the second signal by the controller.

18. The system of claim 17, wherein the user interface is displayed on a desktop computer, an electronic tablet, or a mobile phone.

19. A method of inducing a blink response, the method comprising:

adjusting an electrodynamic layer of a lens between a first state and a second state in response to a first signal by a sensor configured to detect a blink in at least one eye; and adjusting the lens between the second state and the first state in response to a second signal that is generated upon receiving a blink verification by the sensor.

* * * * *